(12) United States Patent
Aurelian et al.

(10) Patent No.: US 8,414,885 B2
(45) Date of Patent: Apr. 9, 2013

(54) METHODS AND COMPOSITIONS FOR TREATING CANCER

(75) Inventors: Laure Aurelian, Baltimore, MD (US);
Aric Colunga, Baltimore, MD (US);
Jennifer Laing, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 69 days.

(21) Appl. No.: 12/853,073

(22) Filed: Aug. 9, 2010

(65) Prior Publication Data
US 2011/0033419 A1 Feb. 10, 2011

Related U.S. Application Data

(60) Provisional application No. 61/232,157, filed on Aug. 7, 2009.

(51) Int. Cl.
*A61K 51/00* (2006.01)
*A61K 39/245* (2006.01)

(52) U.S. Cl. .................................... 424/93.3; 424/229.1

(58) Field of Classification Search .................. None
See application file for complete search history.

(56) References Cited

U.S. PATENT DOCUMENTS
2009/0215147 A1* 8/2009 Zhang et al. ............... 435/235.1
2009/0285860 A1* 11/2009 Martuza et al. ............ 424/277.1

OTHER PUBLICATIONS

Fu et al. Cancer Gene Therapy (2007) 14, 480-487.*
Stinchcombe et al. Cancer Chemother. Pharmacol. 2007, vol. 60 (5), pp. 759-766.*
Fu et al. (Molecular Therapy 2006, 13, No. 5, pp. 882-890).*

* cited by examiner

*Primary Examiner* — Bao Li
(74) *Attorney, Agent, or Firm* — Nevrivy Patent Law Group P.L.L.C.

(57) ABSTRACT

The invention relates to a method of treating cancer, comprising administering to a subject in need thereof an effective amount of a HSV-2 virus, wherein the virus lacks protein kinase activity of ICP10. The invention further relates to pharmaceutical compositions comprising HSV-2 virus, wherein the virus lacks protein kinase activity of ICP10.

12 Claims, 34 Drawing Sheets

Fig. 1B

ΔPK  HSV   R 1    2    3

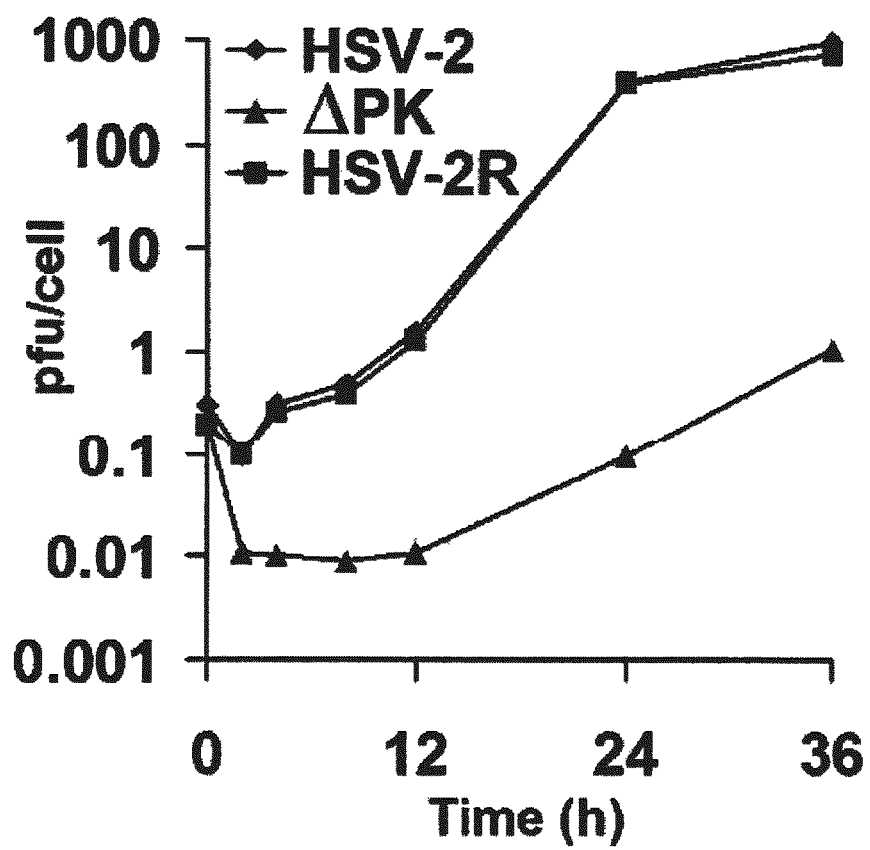

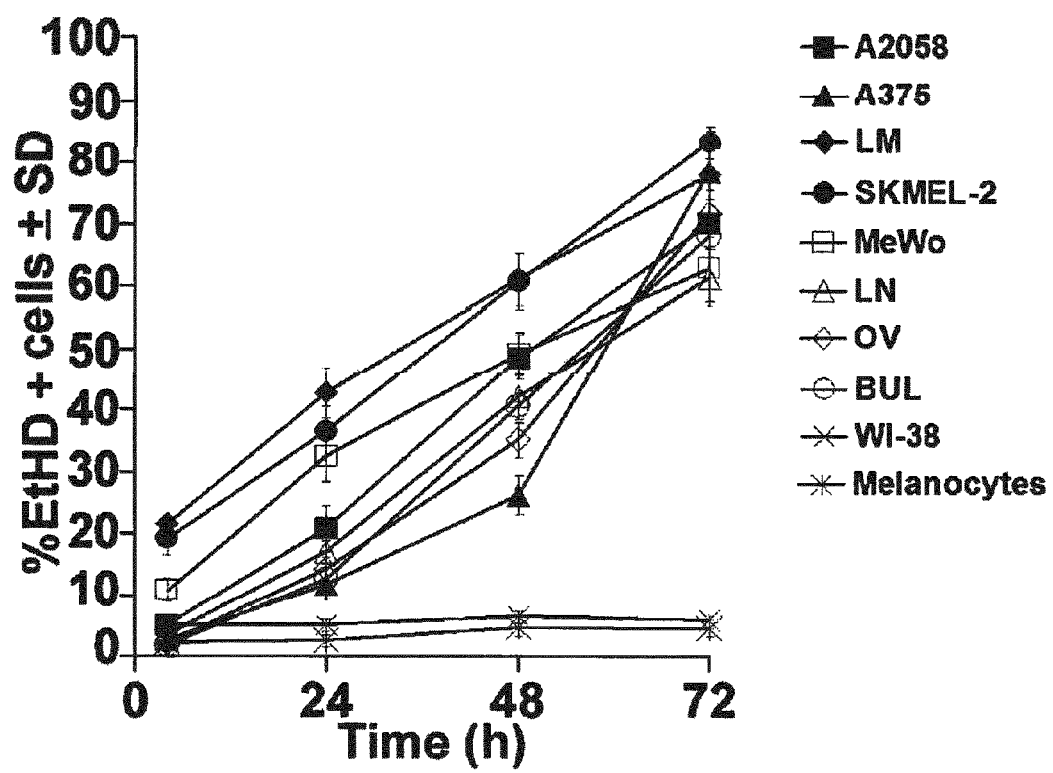

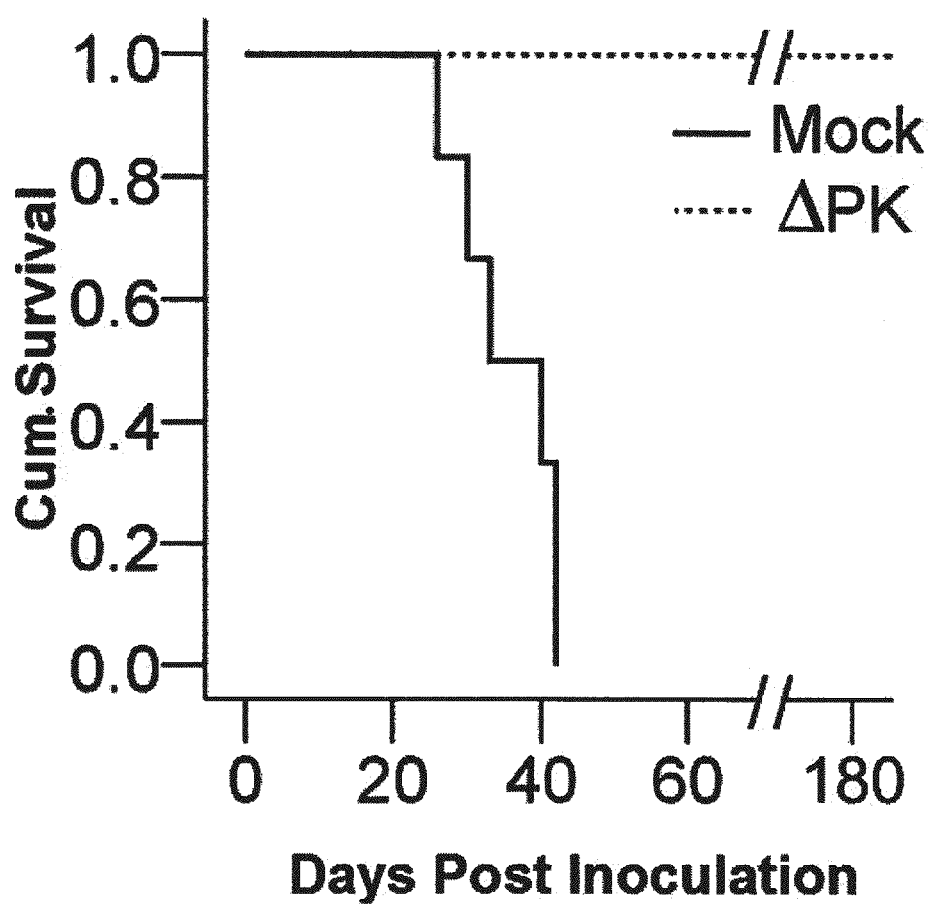

Fig. 15A-C
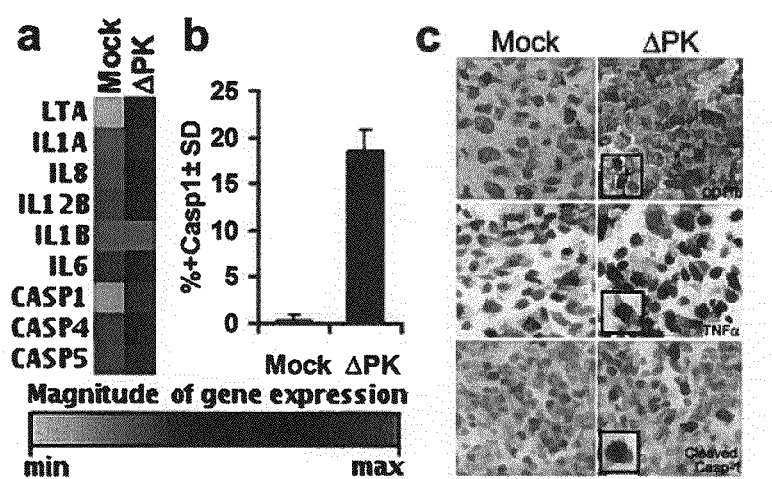

though the tumor (Shen Y, Nemunaitis J. Herpes simplex virus 1 (HSV-1) for cancer treatment. *Cancer Gene Ther* 2006; 13: 975-992; Mathis J M, Stoff-Khalili M A, Curiel D T. Oncolytic adenoviruses—selective retargeting to tumor cells. *Oncogene* 2005; 24: 7775-7791). Virotherapy may also disrupt the tumor vasculature and induce anti-tumor immunity, and virotherapy also carries the promise of targeting cancer stem cells (Shen Y, Nemunaitis J. Herpes simplex virus 1 (HSV-1) for cancer treatment. *Cancer Gene Ther* 2006; 13: 975-992; Mathis J M, Stoff-Khalili M A, Curiel D T. Oncolytic adenoviruses—selective retargeting to tumor cells. *Oncogene* 2005; 24: 7775-7791; Ribacka C, Pesonen S, Hemminki A. Cancer, stem cells, and oncolytic viruses. *Ann Med* 2008; 40: 496-505). Originally developed to target neuronal cancers, the herpes simplex virus (HSV) oncolytic constructs were generated from HSV-1 through deletion/modification of the neurovirulence gene ICP34.5 and/or the large subunit of ribonucleotide reductase (R1). Early clinical trials have shown that oncolytic viral therapies are well tolerated, but their efficacy is modest, apparently related to poor virus replication within the tumors (Aghi M, Martuza R L. Oncolytic viral therapies—the clinical experience. *Oncogene* 2005; 24: 7802-7816). Accordingly, ongoing efforts have focused on improving virus replication through: (i) fusogenic alterations that increase virus uptake/spread; (ii) modulation of the tumor milieu; (iii) suppression of innate immunity or interference with virus-mediated immune evasion; (iv) expression of immunostimulatory cytokines; and (v) use of cytotoxic drugs in combinatorial therapy (Fu X, Tao L, Cai R, Prigge J, Zhang X. A mutant type 2 herpes simplex virus deleted for the protein kinase domain of the ICP10 gene is a potent oncolytic virus. *Mol Ther* 2006; 13: 882-890; Kurozumi K, Hardcastle J, Thakur R, Yang M, Christoforidis G, Fulci G, et al. Effect of tumor microenvironment modulation on the efficacy of oncolytic virus therapy. *J Natl Cancer Inst* 2007; 99: 1768-1781; Fulci G, Breymann L, Gianni D, Kurozomi K, Rhee S S, Yu J, et al. Cyclophosphamide enhances glioma virotherapy by inhibiting innate immune responses. *Proc Natl Acad Sci USA* 2006; 103: 12873-12878; Hu J C, Coffin R S, Davis C J, Graham N J, Groves N, Guest P J, et al. A phase I study of OncoVEXGM-CSF, a second-generation oncolytic herpes simplex virus expressing granulocyte macrophage colony-stimulating factor. *Clin Cancer Res* 2006; 12: 6737-6747; Kumar S, Gao L, Yeagy B, Reid T. Virus combinations and chemotherapy for the treatment of human cancers. *Curr Opin Mol Ther* 2008; 10: 371-379). However, it is becoming increasingly evident that the development of oncolytic viruses with distinct molecular death functions is highly desirable.

It is apparent that there is a need in the art for an effective treatment for cancer (including, for example, melanoma due to this type of cancer's highly aggressive and drug-resistant nature, and due to the fact that there is currently no effective therapy for malignant melanoma) and for the development of efficacious oncolytic viruses.

Malignant melanoma is a highly aggressive and drug-resistant cancer. Virotherapy is a nascent therapeutic strategy based on cancer cell lysis through selective virus replication. However, its clinical efficacy is modest, apparently related to poor virus replication within the tumors. The inventors teach and disclose here for the first time that the growth compromised HSV-2 mutant delta-PK (delta-PK) has strong oncolytic activity for melanoma, which is caused in-part by a mechanism other than replication-induced cell lysis. The invention is drawn to novel methods of treating cancer using

METHODS AND COMPOSITIONS FOR TREATING CANCER

CROSS-REFERENCE TO RELATED APPLICATIONS

This application claims the benefit of provisional U.S. Appl. No. 61/232,157, filed Aug. 7, 2009. The content of the aforesaid application is relied upon and incorporated by reference in its entirety.

STATEMENT REGARDING FEDERALLY SPONSORED RESEARCH OR DEVELOPMENT

This invention was made with government support under Grant Nos. AR053512 and ES007263 awarded by the National Institutes of Health. The government has certain rights in the invention.

REFERENCE TO SEQUENCE LISTING SUBMITTED ELECTRONICALLY

The content of the electronically submitted sequence listing (Name: sequence_listing.txt, Size: 17,277 bytes; and Date of Creation: Aug. 9, 2010) is herein incorporated by reference in its entirety.

BACKGROUND OF THE INVENTION

1. Field of the Invention

The field of the invention relates to cancer biology. The field of the invention further relates to methods of treating cancer.

2. Background of the Invention

Cancer is a group of diseases characterized by uncontrolled cellular growth and, at times, spread of these "abnormal" cells from the initial site of growth to distal areas. If the spread of cancer is not controlled, death can ensue. Cancer is caused by both external factors (e.g., tobacco, infectious organisms, chemicals, and radiation) and internal factors (e.g, inherited mutations, hormones, immune conditions, and mutations that occur from metabolism). These causal factors may act together or in sequence to initiate or promote carcinogenesis. Ten or more years often pass between exposure to external factors and detectable cancer. Cancer is treated with surgery, radiation, chemotherapy, hormone therapy, biological therapy, and targeted therapy. The National Institutes of Health estimates overall costs of cancer in 2008 at $228.1 billion: $93.2 billion for direct medical costs (total of all health expenditures); $18.8 billion for indirect morbidity costs (cost of lost productivity due to illness); and $116.1 billion for indirect mortality costs (cost of lost productivity due to premature death).

There are a number of different types of cancers that affect specific organs or tissues of the body. A particularly prevalent cancer affecting the U.S. population and others worldwide is skin cancer. Malignant melanoma is a commonly diagnosed highly aggressive and drug-resistant cancer that accounts for approximately 75% of cancer skin deaths (Jemal A, Siegel R, Ward E, Murray T, Xu J, Thun M J. Cancer statistics, 2007. *CA Cancer J Clin* 2007; 57: 43-66). Poor prognosis is likely related to the failure of conventional therapies to eradicate cancer cells that are responsible for resistance, invasiveness, and neoplastic progression (Schatton T, Frank M H. Cancer stem cells and human malignant melanoma. *Pigment Cell Melanoma Res* 2008; 21: 39-55). Oncolytic viruses are recognized as a promising novel therapy designed to reduce tumor burden by direct cell lysis resulting from virus replication and generation of infectious progeny that spreads a HSV-2 virus that lacks protein kinase activity of ICP10. An oncolytic virus developed and used by the inventors is HSV-2 ICP10 PK-deleted virus (delta-PK).

BRIEF SUMMARY OF THE INVENTION

In one aspect, the invention is directed to a method of treating cancer, comprising administering to a subject in need thereof an effective amount of a HSV-2 virus, wherein the virus lacks protein kinase activity of ICP10.

In another aspect, the invention is directed to a pharmaceutical composition comprising an effective amount of HSV-2 virus in combination with a pharmaceutically acceptable carrier, diluent and/or additive, wherein the virus lacks kinase activity of ICP10.

DETAILED DESCRIPTION OF THE INVENTION

Figure 1A:
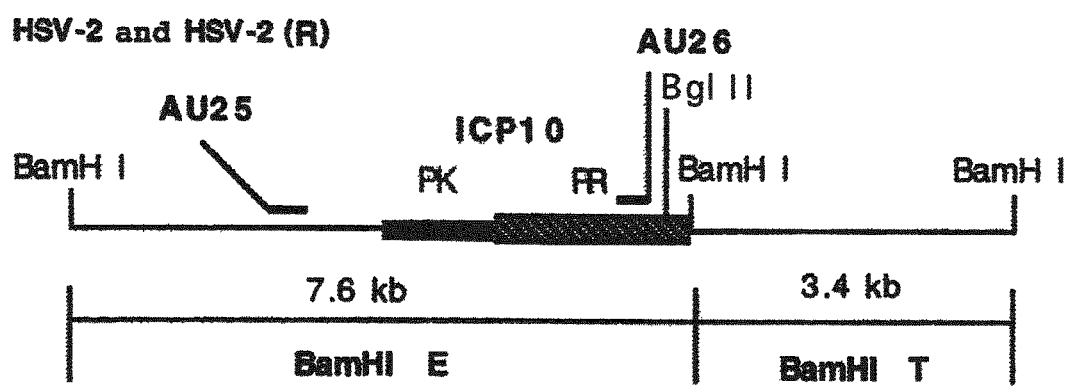
FIG. 1. Delta-PK schematic and detection. A. Schematic representation of ICP10 delta-PK DNA. Oligoprobe AU26 probe should recognize the 7.6 kb BamHI E fragment from HSV-2 or HSV-2(R) DNA and a 2.2 kb BamHI fragment from ICP10 delta-PK DNA. B. Southern blot hybridization of BamH I digested delta-PK (lane 1), HSV-2 (lane 2), or HSV-2 (R) (lane 3).
Figure 1A:
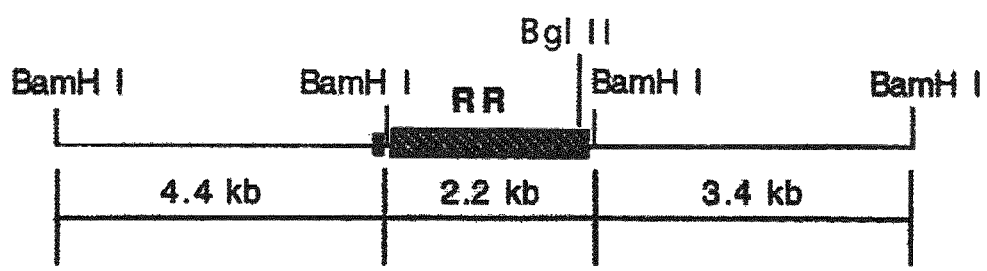

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "treat" and all its forms and tenses (including, for example, treating, treated, and treatment) can refer to therapeutic or prophylactic treatment. In certain aspects of the invention, those in need thereof of treatment include those already with a pathological condition of the invention (including, for example, a cancer), in which case treating refers to administering to a subject (including, for example, a human or other mammal in need of treatment) a therapeutically effective amount of a composition so that the subject has an improvement in a sign or symptom of a pathological condition of the invention. The improvement may be any observable or measurable improvement. Thus, one of skill in the art realizes that a treatment may improve the patient's condition, but may not be a complete cure of the pathological condition. In other certain aspects of the invention, those in need thereof of treatment include, those in which a pathological condition is to be prevented, in which case treating refers to administering a therapeutically effective amount of a composition to a subject (including, for example, a human or other mammal in need of treatment) at risk of developing cancer.

In one aspect, the invention is directed to a method of treating cancer, comprising administering to a subject in need thereof an effective amount of a HSV-2 virus, wherein the virus lacks protein kinase activity of ICP10. The ICP10 gene sequence and amino acid sequence is indicated by SEQ ID NO:1 and SEQ ID NO:2, respectively.

In some embodiments, the virus can be engineered with the UL39 promoter for ICP10 or with mutations within the promoter that would yield reduced protein kinase activities. The ICP10 promoter sequence is indicated by SEQ ID NO:3.

The inventors have found that a HSV-2 kinase deficient mutant of ICP10, delta-PK, effectively and efficiently kills melanoma cells in vitro and in vivo. The inventors have also found that delta-PK has a mechanism of action through activation of functionally distinct proteases (non-redundant PCD pathways) and is associated with upregulation of Beclin-1, H11/HspB and caspase-1-related inflammation.

Oncolytic viruses are engineered and selected to exploit genetic defects in tumor cells that enable selective virus replication. Oncolytic viruses act to reduce tumor burden by infecting tumors and causing cell death (Shen Y, Nemunaitis J. Herpes simplex virus 1 (HSV-1) for cancer treatment. *Cancer Gene Ther* 2006; 13: 975-992; Mathis J M, Stoff-Khalili M A, Curiel D T. Oncolytic adenoviruses—selective retargeting to tumor cells. *Oncogene* 2005; 24: 7775-7791). The therapeutic promise of oncolytic viruses includes the ability to lyse cancer stem cells and stimulate anti-tumor immunity (Schatton T, Frank M H. Cancer stem cells and human malignant melanoma. *Pigment Cell Melanoma Res* 2008; 21: 39-55; Shen Y, Nemunaitis J. Herpes simplex virus 1 (HSV-1) for cancer treatment. *Cancer Gene Ther* 2006; 13: 975-992; Mathis J M, Stoff-Khalili M A, Curiel D T. Oncolytic adenoviruses—selective retargeting to tumor cells. *Oncogene* 2005; 24: 7775-7791; Ribacka C, Pesonen S, Hemminki A. Cancer, stem cells, and oncolytic viruses. *Ann Med* 2008; 40: 496-505). HSV is a particularly promising oncolytic virus because it has a broad host spectrum, is cytolitic, its genome does not integrate into the cellular genome precluding insertion mutagenesis, and antiviral drugs are available to safeguard against unfavorable virus replication. However, cumulative data, including early clinical trials, indicate that the therapeutic benefits of virotherapy are modest (Aghi M, Martuza R L. Oncolytic viral therapies—the clinical experience. *Oncogene* 2005; 24: 7802-7816). Because oncolytic viruses are expected to spread through the tumor mass lysing the cells through productive replication, their limited efficacy was attributed to inhibition of replication by antiviral immunity, incomplete dissemination in the tumor mass, and the failure to replicate in quiescent cells, which may represent a majority of cells in the tumor at any one time (Aghi M, Visted T, Depinho R A, Chiocca E A. Oncolytic herpes virus with defective ICP6 specifically replicates in quiescent cells with homozygous genetic mutations in p16. *Oncogene* 2008; 27: 4249-4254; Yun C O. Overcoming the extracellular matrix barrier to improve intratumoral spread and therapeutic potential of oncolytic virotherapy. *Curr Opin Mol Ther* 2008; 10: 356-361). While ongoing efforts are focused on improving virus replication, it is becoming increasingly evident that the development of oncolytic viruses with distinct molecular death functions is highly desirable.

The present invention follows on recent findings that cancer cell death enhances the penetration and efficacy of oncolytic viruses (Nagano S, Perentes J Y, Jain R K, Boucher Y. Cancer cell death enhances the penetration and efficacy of oncolytic herpes simplex virus in tumors. *Cancer Res* 2008; 68: 3795-3802). These findings are based on the proposition that oncolytic viruses that induce multiple PCD pathways that are not the direct outcome of productive virus replication, have increased therapeutic efficacy and are not subject to the limitations currently ascribed to canonical virotherapy.

In certain aspects, the invention is drawn to treating melanoma, a highly aggressive and drug-resistant cancer of neural crest origin that does not respond to replication-based conventional virotherapy (Vaha-Koskela M J, Kallio J P, Jansson L C, Heikkila J E, Zakhartchenko V A, Kallajoki M A, et al. Oncolytic capacity of attenuated replicative semliki forest virus in human melanoma xenografts in severe combined immunodeficient mice. *Cancer Res* 2006; 66: 7185-7194; MacKie R M, Stewart B, Brown S M. Intralesional injection of herpes simplex virus 1716 in metastatic melanoma. *Lancet* 2001; 357: 525-526), but the invention should not be construed to be this limited. In certain aspects, the invention is drawn to methods of treating cancers of neural crest or CNS origin including glioblastoma other neurological cancers taught herein and known to one of ordinary skill in the art. In other aspects, the invention is drawn to methods of treating cancer in a more general sense.

As used herein, cancer refers to a pathophysiological condition whereby a cell or cells is characterized by dysregulated and/or proliferative cellular growth and the ability to induce said growth, either by direct growth into adjacent tissue through invasion or by growth at distal sites through metastasis, in both, an adult or child, which includes but is not limited to, carcinomas and sarcomas, such as, for example, acute lymphoblastic leukemia, acute myeloid leukemia, adrenocortical cancer, AIDS-related cancers, AIDS-related lymphoma, anal cancer, astrocytoma (including, for example, cerebellar and cerebral), basal cell carcinoma, bile duct cancer, bladder cancer, bone cancer, brain stem glioma, brain tumor (including, for example, ependymoma, medulloblastoma, supratentorial primitive neuroectodermal, visual pathway and hypothalamic glioma), cerebral astrocytoma/malignant glioma, breast cancer, bronchial adenomas/carcinoids, Burkitt's lymphoma, carcinoid tumor (including, for example, gastrointestinal), carcinoma of unknown primary site, central nervous system lymphoma, cervical cancer, chronic lymphocytic leukemia, chronic myelogenous leukemia, chronic myeloproliferative disorders, colon cancer, colorectal cancer, cutaneous T-Cell lymphoma, endometrial cancer, ependymoma, esophageal cancer, Ewing's Family of tumors, extrahepatic bile duct cancer, eye cancer (including, for example, intraocular melanoma, retinoblastoma, gallbladder cancer, gastric cancer, gastrointestinal carcinoid tumor, gastrointestinal stromal tumor (GIST), germ cell tumor (including, for example, extracranial, extragonadal, ovarian), gestational trophoblastic tumor, glioma, hairy cell leukemia, head and neck cancer, squamous cell head and neck cancer, hepatocellular cancer, Hodgkin's lymphoma, hypopharyngeal cancer, islet cell carcinoma (including, for example, endocrine pancreas), Kaposi's sarcoma, laryngeal cancer, leukemia, lip and oral cavity cancer, liver cancer, lung cancer (including, for example, non-small cell), lymphoma, macroglobulinemia, malignant fibrous histiocytoma of bone/osteosarcoma, medulloblastoma, melanoma, Merkel cell carcinoma, mesothelioma, metastatic squamous neck cancer with occult primary, mouth cancer, multiple endocrine neoplasia syndrome, multiple myeloma/plasma cell neoplasm, mycosis fungoides, myelodysplastic syndromes, myelodysplastic/myeloproliferative diseases, myeloma, nasal cavity and paranasal sinus cancer, nasopharyngeal cancer, neuroblastoma, non-Hodgkin's lymphoma, oral cancer, oral cavity cancer, osteosarcoma, oropharyngeal cancer, ovarian cancer (including, for example, ovarian epithelial cancer, germ cell tumor), ovarian low malignant potential tumor, pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, prostate cancer, rectal cancer, retinoblastoma, rhabdomyosarcoma, salivary gland cancer, soft tissue sarcoma, uterine sarcoma, Sézary syndrome, skin cancer (including, for example, non-melanoma or melanoma), small intestine cancer, supratentorial primitive neuroectodermal tumors, T-Cell lymphoma, testicular cancer, throat cancer, thymoma, thymoma and thymic carcinoma, thyroid cancer, transitional cell cancer of the renal pelvis and ureter, trophoblastic tumor (including, for example, gestational), unusual cancers of childhood and adulthood, urethral cancer, endometrial uterine cancer, uterine sarcoma, vaginal cancer, viral induced cancers (including, for example, HPV induced cancer), vulvar cancer, Waldenström's macroglobulinemia, Wilms' Tumor, and women's cancers.

In certain aspects, the invention is drawn treating cancer using delta-PK, an HSV-2 mutant that triggers apoptosis in neurons (Perkins D, Pereira E F, Aurelian L. The herpes simplex virus type 2 R1 protein kinase (ICP10 PK) functions as a dominant regulator of apoptosis in hippocampal neurons involving activation of the ERK survival pathway and upregulation of the antiapoptotic protein Bag-1. *J Virol* 2003; 77: 1292-1305). Delta-PK differs from the recently described HSV-2 oncolytic construct FusOn-H2 in its construction, structure, and biological properties. Delta-PK is deleted in the ICP10 kinase catalytic domain but it retains its transmembrane domain, which is required for membrane localization, protein function, and virion stability (Smith C C, Peng T, Kulka M, Aurelian L. The PK domain of the large subunit of herpes simplex virus type 2 ribonucleotide reductase (ICP10) is required for immediate-early gene expression and virus growth. *J Virol* 1998; 72: 9131-9141; 51. Smith C C, Luo J H, Hunter J C, Ordonez J V, Aurelian L. The transmembrane domain of the large subunit of HSV-2 ribonucleotide reductase (ICP10) is required for protein kinase activity and transformation-related signaling pathways that result in ras activation. *Virology* 1994; 200: 598-612; Luo J H, Aurelian L. The transmembrane helical segment but not the invariant lysine is required for the kinase activity of the large subunit of herpes simplex virus type 2 ribonucleotide reductase (ICP10). *J Biol Chem* 1992; 267: 9645-9653; Smith C C, Aurelian L. The large subunit of herpes simplex virus type 2 ribonucleotide reductase (ICP10) is associated with the virion tegument and has PK activity. *Virology* 1997; 234: 235-242). The kinase deleted ICP10 protein (also known as p95) is present in the virion tegument preserving the structural integrity required for optimal virus uptake and thereby, tumor penetration (Smith C C, Luo J H, Hunter J C, Ordonez J V, Aurelian L. The transmembrane domain of the large subunit of HSV-2 ribonucleotide reductase (ICP10) is required for protein kinase activity and transformation-related signaling pathways that result in ras activation. *Virology* 1994; 200: 598-612). p95 expression is directed by the authentic ICP10 promoter that has IE kinetics and responds to AP-1 transcription factors that regulate genes involved in tumor cell apoptosis (Gober M D, Wales S Q, Hunter J C, Sharma B K, Aurelian L. Stress up-regulates neuronal expression of the herpes simplex virus type 2 large subunit of ribonucleotide reductase (R1; ICP10) by activating activator protein 1. *J Neurovirol* 2005; 11: 329-336; Royuela M, Rodriguez-Berriguete G, Fraile B, Paniagua R. TNF-alpha/IL-1/NF-kappaB transduction pathway in human cancer prostate. *Histol Histopathol* 2008; 23: 1279-1290). Delta-PK does not have any genetic defect other than this deletion, and it has the distinct advantages of: (i) inducing a Th1 response that can override the melanoma Th2-based immunosuppressive milieu; and (ii) being tolerated well in humans (Polak M E, Borthwick N J, Gabriel F G, Johnson P, Higgins B, Hurren J, et al. Mechanisms of local immunosuppression in cutaneous melanoma. *Br J Cancer* 2007; 96: 1879-1887; Gyotoku T, Ono F, Aurelian L. Development of HSV-specific CD4+ Th1 responses and CD8+ cytotoxic T lymphocytes with antiviral activity by vaccination with the HSV-2 mutant ICP10DeltaPK. *Vaccine* 2002; 20: 2796-2807; Minkis K, Kavanagh D G, Alter G, Bogunovic D, O'Neill D, Adams S, et al. Type 2 Bias of T cells expanded from the blood of melanoma patients switched to type 1 by IL-12p70 mRNA-transfected dendritic cells. *Cancer Res* 2008; 68: 9441-9450; Casanova G, Cancela R, Alonzo L, Benuto R, Magana Mdel C, Hurley D R, et al. A double-blind study of the efficacy and safety of the ICP10deltaPK vaccine against recurrent genital HSV-2 infections. *Cutis* 2002; 70: 235-239; Aurelian L. Herpes simplex virus type 2 vaccines: new ground for optimism? *Clin Diagn Lab Immunol* 2004; 11: 437-445; Smith C C, Peng T, Kulka M, Aurelian L. The PK domain of the large subunit of herpes simplex virus type 2 ribonucleotide reductase (ICP10) is required for immediate-early gene expression and virus growth. *J Virol* 1998; 72: 9131-9141; Smith C C, Nelson J, Aurelian L, Gober M, Goswami B B. Ras-GAP binding and phosphorylation by herpes simplex virus type 2 RR1 PK (ICP10) and activation of the Ras/MEK/MAPK mitogenic pathway are required for timely onset of virus growth. *J Virol* 2000; 74: 10417-10429). FusOn-H2 differs from delta-PK in that both the ICP 10PK catalytic and transmembrane domains were replaced with EGFP and the resulting protein was placed under the direction of the promiscuous CMV promoter. In addition, the virus was selected for fusogenic activity imparted by an unrelated and uncharacterized genetic alteration that is credited with improved virus replication within tumor cells and oncolytic activity (Fu X, Tao L, Cai R, Prigge J, Zhang X. A mutant type 2 herpes simplex virus deleted for the protein kinase domain of the ICP10 gene is a potent oncolytic virus. *Mol Ther* 2006; 13: 882-890; Fu X, Tao L, Zhang X. An oncolytic virus derived from type 2 herpes simplex virus has potent therapeutic effect against metastatic ovarian cancer. *Cancer Gene Ther* 2007; 14: 480-487). Although DNA fragmentation with 3'-OH ends (TUNEL) was reported in one FusOn-H2 treated tumor, fusogenic activity is considered to be a critical mechanism of oncolysis, as reflected by the virus name ((Fu X, Tao L, Cai R, Prigge J, Zhang X. A mutant type 2 herpes simplex virus deleted for the protein kinase domain of the ICP10 gene is a potent oncolytic virus. *Mol Ther* 2006; 13: 882-890; Fu X, Tao L, Zhang X. An oncolytic virus derived from type 2 herpes simplex virus has potent therapeutic effect against metastatic ovarian cancer. *Cancer Gene Ther* 2007; 14: 480-487; Fu X, Tao L, Zhang X. An HSV-2-based oncolytic virus deleted in the PK domain of the ICP10 gene is a potent inducer of apoptotic death in tumor cells. *Gene Ther* 2007;

14: 1218-1225). It is apparent that the oncolytic virus of the instant invention is a completely different entity than the FusOn-H2 virus.

Unlike HSV-2 and HSV-2(R) that replicated equally well in all the examined cell types, delta-PK had selective growth potential in cancer/transformed cells. Delta-PK replicated in melanoma and Vero cells, but not in normal fibroblasts (WI-38) and melanocytes. This was not due to the absence of infection, because the % cells staining with antibody to ICP10, which is an IE protein that is expressed in the absence of other viral proteins, was similar to that seen in the melanoma and Vero cultures and consistent with that expected for the used moi (Wymer J P, Chung T D, Chang Y N, Hayward G S, Aurelian L. Identification of immediate-early-type cis-response elements in the promoter for the ribonucleotide reductase large subunit from herpes simplex virus type 2. *J Virol* 1989; 63: 2773-2784; Knipe D M, Fields B N, Howley P M, Griffin D, Lamb R, Martin M A. *Fields' virology*. Philadelphia, Pa.: Wolters Kluwer Health/Lippincott Williams & Wilkins, c2007.: 2007, pp 86). The maximal levels of virus growth in the melanoma cultures was significantly lower than that of delta-PK induced cell death, with a trypan blue+ or EtHD+/VP5+ ratio of 1.8-4.1 for the different cultures at 24-72 hrs p.i. and similar results were obtained for melanoma cultures with distinct patterns of activated survival/proliferation pathways. Because VP5 staining is a marker of infectious progeny production, the data suggest that cell death was primarily due to a program other than lysis caused by productive virus growth (bystander effect). Without being bound by theory, it is believed that the bystander effect was due to activation of non-redundant death programs because: (i) calpain and caspases-7 and -3 were activated in delta-PK infected cultures, but not mock-infected cultures; and (ii) cell death was reduced by the calpain inhibitor PD150606 or the pancaspase inhibitor z-VAD-fmk (used at previously established effective doses), but it was only abrogated by the combination of both inhibitors. Calpain activation was first seen at 1 hr p.i., when it presented as an increased p76/p80 ratio. It increased with time and, by 24 hrs p.i., was accompanied by the loss of the regulatory p28 subunit. Interestingly, while caspases-7 and -3 generally compensate for each other and are not simultaneously activated, the present inventors have found that both were activated by delta-PK. Activation of caspase-7, was first seen at 4 hrs p.i. and it increased with time, such that by 24 hrs p.i, the p20 cleavage fragment was replaced by the lower fragments p17 and p11. Caspase-3 activation was not seen before 24 hrs p.i. This is consistent with recent reports that these two caspases are differentially activated and they have distinct functions/targets, such that maximal cell death is only seen when both are simultaneously activated (Walsh J G, Cullen S P, Sheridan C, Luthi A U, Gerner C, Martin S J. Executioner caspase-3 and caspase-7 are functionally distinct proteases. *Proc Natl Acad Sci USA* 2008; 105: 12815-12819; Lamkanfl M, Kanneganti T D, Van Damme P, Vanden Berghe T, Vanoverberghe I, Vandekerckhove J, et al. Targeted peptidecentric proteomics reveals caspase-7 as a substrate of the caspase-1 inflammasomes. *Mol Cell Proteomics* 2008; 7: 2350-2363; Sung Y H, Lee J S, Park S H, Koo J, Lee G M. Influence of co-down-regulation of caspase-3 and caspase-7 by siRNAs on sodium butyrate-induced apoptotic cell death of Chinese hamster ovary cells producing thrombopoietin. *Metab Eng* 2007; 9: 452-464).

Apoptosis is the best studied PCD and it involves both caspase-dependent extrinsic and intrinsic pathways (Aurelian L. HSV-induced apoptosis in herpes encephalitis. *Curr Top Microbiol Immunol* 2005; 289: 79-111). However, canonical apoptosis (measured by TUNEL+ cells) was a relatively small component of the delta-PK induced cell death. Caspase-independent death pathways were also reported, for example through AIF release from mitochondria and its translocation to the nucleus, as was death caused by both caspase-dependent and independent pathways or by distinct PCD pathways, such as autophagy (Chu C T, Zhu J H, Cao G, Signore A, Wang S, Chen J. Apoptosis inducing factor mediates caspase-independent 1-methyl-4-phenylpyridinium toxicity in dopaminergic cells. *J Neurochem* 2005; 94: 1685-1695; Wales S Q, Laing J M, Chen L, Aurelian L. ICP10PK inhibits calpain-dependent release of apoptosis-inducing factor and programmed cell death in response to the toxin MPP+. *Gene Ther* 2008; 15: 1397-1409; 60. Choi W S, Lee E H, Chung C W, Jung Y K, Jin B K, Kim S U, et al. Cleavage of Bax is mediated by caspase-dependent or -independent calpain activation in dopaminergic neuronal cells: protective role of Bcl-2. *J Neurochem* 2001; 77: 1531-1541; Han B S, Hong H S, Choi W S, Markelonis G J, Oh T H, Oh Y J. Caspase-dependent and -independent cell death pathways in primary cultures of mesencephalic dopaminergic neurons after neurotoxin treatment. *J Neurosci* 2003; 23: 5069-5078; Shacka J J, Roth K A, Zhang J. The autophagy-lysosomal degradation pathway: role in neurodegenerative disease and therapy. *Front Biosci* 2008; 13: 718-736). Calpains are Ca2+-dependent neutral cysteine proteases, the relationship of which to the caspases is still poorly understood. Some reports suggest that calpains act independently of the caspases in different PCD pathways, while others conclude that they cooperate. In the latter case, calpain activation was found to follow or initiate the activation of the caspases (Wales S Q, Laing J M, Chen L, Aurelian L. ICP10PK inhibits calpain-dependent release of apoptosis-inducing factor and programmed cell death in response to the toxin MPP+. *Gene Ther* 2008; 15: 1397-1409; Gao G, Dou Q P. N-terminal cleavage of bax by calpain generates a potent proapoptotic 18-kDa fragment that promotes bcl-2-independent cytochrome C release and apoptotic cell death. *J Cell Biochem* 2000; 80: 53-72). Calpain cleavage of caspase-9 and caspase-3 was reported to attenuate or facilitate their activity during apoptosis, but more recent data suggest that calpains function in caspase-independent PCD (42. Bizat N, Hermel J M, Humbert S, Jacquard C, Creminon C, Escartin C, et al. In vivo calpain/caspase cross-talk during 3-nitropropionic acid-induced striatal degeneration: implication of a calpain-mediated cleavage of active caspase-3. *J Biol Chem* 2003; 278: 43245-43253; Neumar R W, Xu Y A, Gada H, Guttmann R P, Siman R. Cross-talk between calpain and caspase proteolytic systems during neuronal apoptosis. *J Biol Chem* 2003; 278: 14162-14167; Choi W S, Lee E H, Chung C W, Jung Y K, Jin B K, Kim S U, et al. Cleavage of Bax is mediated by caspase-dependent or -independent calpain activation in dopaminergic neuronal cells: protective role of Bcl-2. *J Neurochem* 2001; 77: 1531-1541; Takano J, Tomioka M, Tsubuki S, Higuchi M, Iwata N, Itohara S, et al. Calpain mediates excitotoxic DNA fragmentation via mitochondrial pathways in adult brains: evidence from calpastatin mutant mice. *J Biol Chem* 2005; 280: 16175-16184; Cao G, Xing J, Xiao X, Liou A K, Gao Y, Yin X M, et al. Critical role of calpain I in mitochondrial release of apoptosis-inducing factor in ischemic neuronal injury. *J Neurosci* 2007; 27: 9278-9293.). Because activation of calpain and caspase-7 preceded the onset of delta-PK replication while activation of caspase-3 was a relatively late event, the inventors believe, without being bound by theory, that distinct virus functions are involved in the activation of the three proteases, at least some of which are independent of a fully productive replicative cycle. In this context it is important to point out that expression of the IE gene ICP0 was shown to act as an initial inducer of apoptosis, but the contribution of cellular genes that are likely upregulated by distinct virus functions, cannot be excluded (Sanfilippo C M, Blaho J A. ICP0 gene expression is a herpes simplex virus type 1 apoptotic trigger. *J Virol* 2006; 80: 6810-6821; Mahller Y Y, Sakthivel B, Baird W H, Aronow B J, Hsu Y H, Cripe T P, et al. Molecular analysis of human cancer cells infected by an oncolytic HSV-1 reveals multiple upregulated cellular genes and a role for SOCS1 in virus replication. *Cancer Gene Ther* 2008; 15: 733-741).

Significantly, delta-PK had robust oncolytic activity in melanoma xenografts. The virus was given at a relatively low dose ($10^6$-$10^7$ pfu). The studies taught and described herein demonstrate that tumor growth was inhibited in all cases with virtually absolute survival (80-100%). In the case of the LM xenografts, complete remission was seen for ⅞ tumors (87.5%), followed for 5 months after the last delta-PK injection and the lone recurrent tumor did not reach endpoint criteria (1.5 cm in diameter) by this time.

Analysis of the delta-PK treated xenografts at 7 days after the last injection indicated that a small number of well distributed cells stained with VP5 antibody and the tissues were positive for low titers of infectious virus, indicative of sustained virus replication and relatively good levels of tumor penetration. As was the case for the melanoma cultures, the delta-PK treated xenografts were positive for activated calpain and caspase-7 and caspase-3. Interestingly, they also evidenced upregulation of Beclin-1 and H11/HspB. In addition, the delta-PK treated xenografts were also positive for activated caspase-1 and evidenced increased levels of the pro-inflammatory cytokine TNF-alpha and infiltrating CD11b+ cells (macrophages). In this context, it is important to point out that the caspase-1 antibody used in these studies is specific for the human protein, suggesting that the activated caspase-1 detected in the delta-PK treated xenografts is of melanoma, rather than macrophage origin. The exact contribution of these death-related proteins to melanoma oncolysis is still unclear, but presently available data underscore their potential cross-talk with caspase and/or calpain-induced PCD. Autophagy is a process of self-digestion that was reported to cause or protect against cell death and calpain can cleave autophagy proteins, thereby providing a switch between autophagy and apoptosis (Luo S, Rubinsztein D C. Atg5 and Bcl-2 provide novel insights into the interplay between apoptosis and autophagy. *Cell Death Differ* 2007; 14: 1247-1250; White E. Autophagic cell death unraveled: Pharmacological inhibition of apoptosis and autophagy enables necrosis. *Autophagy* 2008; 4: 399-401; Levine B, Sinha S, Kroemer G. Bcl-2 family members: dual regulators of apoptosis and autophagy. *Autophagy* 2008; 4: 600-606). The critical autophagy protein Beclin-1 was associated with cell death involving cross-talk with Bcl-2 family members and it acts as a haploinsufficient tumor suppressor protein that is downregulated in human tumors (Qu X, Yu J, Bhagat G, Furuya N, Hibshoosh H, Troxel A, et al. Promotion of tumorigenesis by heterozygous disruption of the beclin 1 autophagy gene. *J Clin Invest* 2003; 112: 1809-1820; Miracco C, Cosci E, Oliveri G, Luzi P, Pacenti L, Monciatti I, et al. Protein and mRNA expression of autophagy gene Beclin 1 in human brain tumours. *Int J Oncol* 2007; 30: 429-436; Levine B, Sinha S, Kroemer G. Bcl-2 family members: dual regulators of apoptosis and autophagy. *Autophagy* 2008; 4: 600-606). Pyroptosis is a caspase-1 dependent inflammatory form of cell death that involves formation of the inflammasome complex and was originally observed in macrophages (Fernandes-Alnemri T, Wu J, Yu J W, Datta P, Miller B, Jankowski W, et al. The pyroptosome: a supramolecular assembly of ASC dimers mediating inflammatory cell death via caspase-1 activation. *Cell Death Differ* 2007; 14: 1590-1604; Yu H B, Finlay B B. The caspase-1 inflammasome: a pilot of innate immune responses. *Cell Host Microbe* 2008; 4: 198-208). TNF-alpha, a pro-apoptotic inflammatory cytokine is a death signal and it slows the growth of some tumors (Villeneuve J, Tremblay P, Vallieres L. Tumor necrosis factor reduces brain tumor growth by enhancing macrophage recruitment and microcyst formation. *Cancer Res* 2005; 65: 3928-3936). TNF-alpha can also activate caspase-1 and caspase-7 is a caspase-1 substrate (Jain N, Sudhakar C, Swarup G. Tumor necrosis factor-alpha-induced caspase-1 gene expression. Role of p'73. *FEBS J* 2007; 274: 4396-4407; Lamkanfi M, Kanneganti T D, Van Damme P, Vanden Berghe T, Vanoverberghe I, Vandekerckhove J, et al. Targeted peptidecentric proteomics reveals caspase-7 as a substrate of the caspase-1 inflammasomes. *Mol Cell Proteomics* 2008; 7: 2350-2363). The finding that these death-associated factors co-exist with protease activation suggests that they are likely to be independently upregulated/activated by delta-PK and contribute to oncolysis in vivo, possibly through a positive feedback amplification loop. However, because in cultured cells oncolysis is abolished through caspase and calpain inhibition, we cannot exclude the possibility that Beclin-1, H11/HspB8 and the inflammatory processes function downstream of calpain and/or caspase. Infectious virus and VP5 staining were not seen in the liver tissues collected at the end of the experimental procedure indicating that there was no systemic toxicity. To corroborate the safety of delta-PK, clinical trials have demonstrated that this virus is well tolerated (Casanova G, Cancela R, Alonzo L, Benuto R, Magana Mdel C, Hurley D R, et al. A double-blind study of the efficacy and safety of the ICP10deltaPK vaccine against recurrent genital HSV-2 infections. *Cutis* 2002; 70: 235-239; Aurelian L. Herpes simplex virus type 2 vaccines: new ground for optimism? *Clin Diagn Lab Immunol* 2004; 11: 437-445).

Collectively, the data demonstrate that delta-PK is a promising treatment for cancer (including, for example, melanoma) virotherapy strategy in which the relatively limited virus replication is associated with a robust tumor cell killing bystander effect mediated by alternative PCD programs. To this end, the present invention provides a novel, nonobvious, and efficacious method for treating cancer.

In certain aspects of the invention, methods of treating cancer comprising administering a HSV-2 virus, wherein the virus lacks protein kinase activity of ICP10, such as delta-PK, can be combined with other methods of treating cancer. Other methods of treating cancer, include but is not limited to, surgical therapy, radiation therapy, administering an anticancer agent (including, for example, antineoplastics or combinations thereof, and angiogenesis inhibitors), immunotherapy, antineoplastons, investigational drugs, vaccines, less conventional therapies (sometimes referred to as novel or innovative therapies, which include, for example, chemoembolization, hormone therapy, local hyperthermia, photodynamic therapy, radiofrequency ablation, stem cell transplantation, and gene therapy), prophylactic therapy (including, for example, prophylactic mastectomy or prostatectomy), alternative and complementary therapies (including, for example, dietary supplements, megadose vitamins, herbal preparations, special teas, physical therapy, acupuncture, massage therapy, magnet therapy, spiritual healing, meditation, pain management therapy, and naturopathic therapy (including, for example, botanical medicine, homeopathy, Chinese medicine, and hydrotherapy)), and a combination of more than one of any of the foregoing.

In certain aspects of the invention drawn to administering a HSV-2 virus, wherein the virus lacks protein kinase activity of ICP10, such as delta-PK, with an anticancer agent, an anticancer agent includes, for example, Abraxane, Aldara, Alimta, Aprepitant, Arimidex, Aromasin, Arranon, Arsenic Trioxide, Avastin, Bevacizumab, Bexarotene, Bortezomib, Cetuximab, Clofarabine, Clofarex, Clolar, Dacogen, Dasatinib, Ellence, Eloxatin, Emend, Erlotinib, Faslodex, Femara, Fulvestrant, Gefitinib, Gemtuzumab Ozogamicin, Gemzar, Gleevec, Herceptin, Hycamtin, Imatinib Mesylate, Iressa, Kepivance, Lenalidomide, Levulan, Methazolastone, Mylosar, Mylotarg, Nanoparticle Paclitaxel, Nelarabine, Nexavar, Nolvadex, Oncaspar, Oxaliplatin, Paclitaxel, Paclitaxel Albumin-stabilized Nanoparticle Formulation, Palifermin, Panitumumab, Pegaspargase, Pemetrexed Disodium, Platinol-AQ, Platinol, Revlimid, Rituxan, Sclerosol Intrapleural Aerosol, Sorafenib Tosylate, Sprycel, Sunitinib Malate, Sutent, Synovir, Tamoxifen, Tarceva, Targretin, Taxol, Taxotere, Temodar, Temozolomide, Thalomid, Thalidomide, Topotecan Hydrochloride, Trastuzumab, Trisenox, Vectibix, Velcade, Vidaza, Vorinostat, Xeloda, Zoledronic Acid, Zolinza, Zometa, doxorubicin, adriamycin, bleomycin, daunorubicin, dactinomycin, epirubicin, idarubicin, mitoxantrone, valrubicin, hydroxyurea, mitomycin, fluorouracil, 5-FU, methotrexate, floxuridine, interferon alpha-2b, glutamic acid, plicamycin, 6-thioguanine, aminopterin, pemetrexed, raltitrexed, cladribine, clofarabine, fludarabine, mercaptopurine, pentostatin, capecitabine, cytarabine, carmustine, BCNU, lomustine, CCNU, cytosine arabinoside, cyclophosphamide, estramustine, hydroxyurea, procarbazine, mitomycin, busulfan, medroxyprogesterone, estramustine phosphate sodium, ethinyl estradiol, estradiol, megestrol acetate, methyltestosterone, diethylstilbestrol diphosphate, chlorotrianisene, testolactone, mephalen, mechlorethamine, chlorambucil, chlormethine, ifosfamide, bethamethasone sodium phosphate, dicarbazine, asparaginase, mitotane, vincristine, vinblastine, etoposide, teniposide, Topotecan, IFN-gamma, irinotecan, campto, irinotecan analogs, carmustine, fotemustine, lomustine, streptozocin, carboplatin, oxaliplatin, BBR3464, busulfan, dacarbazine, mechlorethamine, procarbazine, thioTEPA, uramustine, vindesine, vinorelbine, alemtuzumab, tositumomab, methyl aminolevulinate, porfimer, verteporfin, lapatinib, nilotinib, vandetanib, ZD6474, alitretinoin, altretamine, amsacrine, anagrelide, denileukin diftitox, estramustine, hydroxycarbamide, masoprocol, mitotane, tretinoin, or other anticancer agents, including, for example, antibiotic derivatives, cytotoxic agents, angiogenesis inhibitors, hormones or hormone derivatives, nitrogen mustards and derivatives, steroids and combinations, and antimetbolites. In further particular aspects of the invention, an anticancer agent comprises two or more of the foregoing anticancer agents.

In certain aspects of the invention drawn to administering a HSV-2 virus, wherein the virus lacks protein kinase activity of ICP10, such as delta-PK, with a combination of anticancer agents, a combination of anticancer agents includes, for example, CHOP (Cytoxan, Hydroxyrubicin (Adriamycin), Oncovin (Vincristine), Prednisone), CHOP-R (CHOP, rituximab), FOLFOX (Fluorouracil, leucovorin (folinic acid), oxaliplatin), VAD (Vincristine, Adriamycin (doxorubicin), dexamethasone), Thal/Dex (Thalidomide, dexamethasone), COP or CVP (Cyclophosphamide, vincristine (Oncovin), and prednisone), m-BACOD (Methotrexate, bleomycin, doxorubicin (Adriamycin), cyclophosphamide, vincristine (Oncovin), dexamethasone (Decadron)), ProMACE-CytaBOM (Prednisone, doxorubicin (adriamycin), cyclophosphamide, etoposide, cytarabine, bleomycin, vincristine (Oncovin), methotrexate, leucovorin), COPP (Cyclophosphamide, Oncovin (vincristine), procarbazine, prednisone), MACOP-B (Methotrexate, leucovorin, doxorubicin (Adriamycin), cyclophosphamide, vincristine (Oncovin), prednisone, bleomycin), MOPP (Mechlorethamine, vincristine (oncovin), procarbazine, prednisone), ProMACE-MOPP (Methotrexate, doxorubicin (Adriamycin), cyclophosphamide, etoposide, MOPP), ABVD (Adriamycin, bleomycin, vinblastine, dacarbazine), BEACOPP (Bleomycin, etoposide, Adriamycin (doxorubicin), cyclophosphamide, Oncovin (vincristine), procarbazine, prednisone), Stanford V (Doxorubicin (Adriamycin), mechlorethamine, bleomycin, vinblastine, vincristine (Oncovin), etoposide (VP-16), prednisone), ECF (Epirubicin, cisplatin, fluorouracil), BEP (Bleomycin, etoposide, platinum (cisplatin)), and PCV (Procarbazine, lomustine (CCNU), vincristine).

In certain aspects of the invention drawn to administering a HSV-2 virus, wherein the virus lacks protein kinase activity of ICP10, such as delta-PK, alone or in combination as described herein, routes of administration include, for example, intraarterial administration, epicutaneous administration, eye drops, intranasal administration, intragastric administration (e.g., gastric tube), intracardiac administration, subcutaneous administration, intraosseous infusion, intrathecal administration, transmucosal administration, epidural administration, insufflation, oral administration (e.g., buccal or sublingual administration), oral ingestion, anal administration, inhalation administration (e.g., via aerosol), intraperitoneal administration, intravenous administration, transdermal administration, intradermal administration, subdermal administration, intramuscular administration, intrauterine administration, vaginal administration, administration into a body cavity, surgical administration (e.g., at the location of a tumor or internal injury), administration into the lumen or parenchyma of an organ, or other topical, enteral, mucosal, parenteral administration, or other method or any combination of the forgoing as would be known to one of ordinary skill in the art (see, for example, Remington's Pharmaceutical Sciences, 18th Ed. Mack Printing Company, 1990, incorporated herein by reference). In particular aspects of the invention drawn to administering delta-PK alone or in combination as described herein, delta-PK is administered topically or transdermally.

As used herein, an effective amount of HSV-2 virus, wherein the virus lacks protein kinase activity of ICP10, encompasses an amount that can kill cancer cells and lead to a measurable reduction in the extent of the tumor or number of cancer cells in the subject. In some embodiments, effective amounts range from about $1 \times 10^4$ to about $4 \times 10^{12}$ PFU of virus per kilogram of body weight of the subject to be treated. In some embodiments, for systemic treatment, doses can range from about $1 \times 10^5$ to about $4 \times 10^8$ PFU per kilogram. It is understood by those skilled in the art that the dose of virus that must be administered will vary depending on, for example, the subject which will receive the virus, the type of cancer, the extent of cancer cell growth or metastasis, the biological site or body compartment of the tumor(s), the route of administration, and the identity of any other drugs or treatment being administered to the subject, such as anti-cancer drugs, radiation, chemotherapy, or surgical treatment. It is also understood that it may be necessary to give more than one dose of the virus. The optimal interval between such multiple doses of virus can be determined empirically and is within the skill of the art.

In another aspect, the invention is directed to a pharmaceutical composition comprising an effective amount of HSV-2 virus in combination with a pharmaceutically acceptable carrier, diluent and/or additive, wherein the virus lacks kinase activity of ICP10.

Any of a number of well-known formulations for introducing viruses into cells in subjects, such as humans, can be used in the invention. (See, e.g., Remington's Pharmaceutical Sciences (18th edition), ed. A. Gennaro, 1990, Mack Publishing Co., Easton, Pa.). However, the viruses can be simply diluted in a physiologically acceptable solution, such as sterile saline or sterile buffered saline.

The administration can be achieved in a single dose or repeated at intervals, as determined to be appropriate by those of skill in this art.

While the invention has been described with reference to certain particular aspects or embodiments thereof, those skilled in the art will appreciate that various modifications may be made without departing from the spirit and scope of the invention. The scope of the invention is not to be limited to the specific aspects or embodiments described herein.

EXAMPLES

Example 1

Cells and Viruses

Melanoma cell lines A2058, A375, MeWo and SKMEL-2 were obtained from the American Type Culture Collection (Manassas, Va.) and grown in Dulbeco's modified Eagle's medium (DMEM) with 10% fetal bovine serum (FBS, Gemini Bioproducts, Calabasos, Calif.). For A375, A2058 and MeWo, the medium was supplemented with 4.5 g/L glucose, 1500 mg/ml sodium bicarbonate, and 4 mM glutamine. Melanoma cultures LM, SM, LN, OV, and BUL were established from histologically confirmed metastatic melanomas and passaged only 4-6 times prior to study. SM, LN, OV, and BUL were obtained from Dr. G. Elias (Franklin Square Hospital, Baltimore Md.) and cultured in Iscove's Modified Dulbecco's Medium. LM were obtained from Dr. Joseph Sinkovics (University of South Florida, Tampa, Fla.) and cultured in RPMI 1640 medium with 10% FBS. Adult primary melanocytes (Cascade Biologics/Invitrogen, Portland, Oreg.) were grown in Medium 254 supplemented with 0.5% fetal bovine serum, 3 ng/ml basic fibroblast growth factor, 0.2% bovine pituitary extract, 3 µg/ml heparin, 0.18 µg/ml hydrocortisone, 5 µg/ml insulin, 5 µg/ml transferrin, and 10 nM endothelin-1 (human melanocyte supplement—2 from Cascade Biologics). WI-38 cells (normal human embryonic lung fibroblasts) are an expansion from passage 9 and have a limited lifespan of 50 population doublings. Vero cells (African green monkey kidney) were used at a relatively late passage (>150) at which they evidence transformation-related properties and tumor formation (36). WI-38 and Vero cells were cultured in minimal essential medium (MEM) with Earle's salts, 10% FBS, 1 mM sodium pyruvate, 0.1 mM non-essential amino acids.

The generation and properties of the HSV-2 mutant delta-PK and the revertant virus HSV-2(R) were previously described (Smith C C, Peng T, Kulka M, Aurelian L. The PK domain of the large subunit of herpes simplex virus type 2 ribonucleotide reductase (ICP10) is required for immediate-early gene expression and virus growth. *J Virol* 1998; 72: 9131-9141). Delta-PK is deleted in the sequences that encode the kinase function of ICP10 (also known as HSV-2 R1). The ICP10 kinase activity functions independently of the R1 activity and is required for virus growth. Delta-PK expresses the kinase negative (ICP10PK deleted) protein p95 under the direction of the authentic immediate early (IE) ICP10 promoter (Id.). Delta-PK was grown in Vero cells. Cell lysates were cleared of cell debris by centrifugation at 3,000×g for 10 min. Virus was used as is or further partially purified by centrifugation of the cell lyates at 113,000×g for 1 hr followed by resuspension in MEM with Earle's salts, 1 mM sodium pyruvate, and 0.1 mM non-essential amino acids, as previously described (Sheridan J F, Beck M, Smith C C, Aurelian L. Reactivation of herpes simplex virus is associated with production of a low molecular weight factor that inhibits lymphokine activity in vitro. *J Immunol* 1987; 138: 1234-1239).

Example 2

Construction and Characterization of the Delta-PK Virus and HSV-2(R)

The construction of the delta-PK virus has been described (U.S. Pat. No. 6,013,265; U.S. Pat. No. 6,054,131; U.S. Pat. No. 7,482,318; Peng et al., Virology 216:184-196, 1996). Briefly, for example, the wild type sequences in a plasmid (e.g., TP101) that contains the HSV-2 BamHI E and T fragments were replaced with the 1.8 kb SalI/BglII fragment from pJHL9 [ICP10 mutant deleted in the PK catalytic domain, lacking amino acids 106-445 (Luo and Aurelian, J. Biol. Chem. 267:9645-9653, 1992)]. The resulting plasmid, TP9, contains sequences which code for ICP10 deleted in the PK catalytic domain flanked by 4 and 2.8 kb of HSV-2 DNA sequences at the 5' and 3' ends, respectively. The 10 kb HindIII/EcoR1 fragment from TP9 was introduced by marker transfer into a virus (ICP10.DELTA.RR) in which the RR domain of ICP10 had been replaced with the LacZ gene. The resulting recombinant virus, designated delta-PK, was obtained by selecting white plaques on a background of blue plaques after staining with X-gal. A few white plaques were picked, purified, and grown in Vero cells in MEM with 10% FCS (exponential). For the construction of the restored virus HSV-2(R), Vero cells were co-tranfected with 1 .mu.g of infectious viral DNA from delta-PK and a 10-fold molar excess of the wild type BamHI E/T fragment. A strategy similar to that reported for ICP6.DELTA. (Goldstein and Weller, Virology 166:41-51, 1988b) was used to select restored virus under growth restricted conditions (serum starved Vero cells).

Southern blot hybridization was used to confirm that the ICP10 delta-PK DNA is deleted in the ICP10 PK coding region. Generally, viral DNA was isolated from cytoplasmic virions as described (Pignatti et al., Virology 93:260-264, 1979; Smith et al., J. Gen. Virol. 73:1417-1428, 1992a). Briefly, Vero cells were infected at a multiplicity of infection (moi) of 5. At 48 hrs. p.i. cells were resuspended ($2 \times 10^7$ cells/ml) in a buffer consisting of 10 mM Tris-HCl (pH 7.9), 10 mM EDTA and 0.25% Triton. Following incubation on ice, NaCl was added at a final concentration of 0.2M and the nuclei were precipitated by centrifugation at 1,000×g (10 min, 4 degrees C.). The supernatant, containing cytoplasmic virions, was incubated in 200 .mu.g/ml Proteinase K and 0.2% SDS (4 hr at 37 degrees C.), mixed with saturated sodium iodide (NaI; final concentration 1.525 g/ml) and ethidium bromide (final concentration 3 µg/ml) and centrifuged at 100,000×g for 16 hrs Viral DNA (15 µg) was digested with BamH I and the fragments were separated by 1% agarose gel electrophoresis in a Tris-Acetate-EDTA (TAE) buffer (40 mM Tris-acetate and 1 mM EDTA). It was transferred to GENE SCREEN membranes (New England Nuclear Corp.) and the membranes were incubated in a prehybridization solution containing 5×SSC [750 mM NaCl, 75 mM Sodium citrate; pH (7.0)], 2% Casein, 0.1% N-laurylsarcosine and 0.02% sodium dodecyl sulfate (SDS)] at 42 degrees C. for 2 hrs. The hybridization probe was oligonucleotide AU26 (CCCCTTCATCAT-GTTTAAGGA) (SEQ ID NO: 4) which represents a sequence in the ICP10 RR coding region. It was 3' tailed with Digoxigenin-dUTP (DIG-dUTP) by terminal transferase (Boehringer Mannheim) in 20 µl volume with 1× reaction buffer [5 mM cobalt chloride ($CoCl_2$), 0.05 mM DIG-dUTP, 5 nmol/ml AU26, 0.5 mM dATP and 2.5 units/µl terminal tranferase] at 37 degrees C. for 15 min. diluted to a final concentration of 5 pmol/ml in prehybridization solution. Hybridization was done at 42 degrees C. for 3 hrs. Membranes were washed once (room temperature) in a solution containing 2×SSC, 0.1% SDS for 5 min. and twice in 0.5×SSC, 0.1% SDS for 15 mins. For detection of the hybridized DNA fragments, the membranes were rinsed in Buffer 1 (100 mM Tris-HCl, pH 7.5, 150 mM NaCl), incubated in Buffer 2 [2% (w/v) casein in Buffer 1] for 40 min and in Buffer 2 containing $3 \times 10^4$ U/ml of alkaline phosphatase-conjugated anti-digoxigenin antibody (Boehringer Mannheim) for 30 min. After washing with Buffer 1 (twice) and soaking in Buffer 3 (100 mM Tris-HCl, pH 9.5, 100 mM NaCl, 50 mM $MgCl_2$) for 2 min, the membranes were exposed to the chemiluminescent substrate LUMI-PHOS 530 (Boehringer Mannheim) and the reaction was developed on X-ray film.

More specifically, DNA (15 µg) from delta-PK or HSV-2 (R) was digested with BamHI, separated on 1% agarose gels and transferred to nylon membranes. It was hybridized with the AU26 probe which recognizes a sequence within the ICP10 RR coding region (FIG. 1A). A hybridizing 7.6 kb band which represents the BamHI E fragment was observed for HSV-2, (FIG. 1B, lane 2) and HSV-2(R) (FIG. 1B, lane 3) DNA. The hybridizing band seen for ICP10 delta-PK DNA was 2.2 kb (FIG. 1B, lane 1) consistent with the expected size. The data confirm that ICP10 delta-PK DNA is deleted in the PK coding region.

Example 3

Antibodies, Pharmacological Inhibitors and Chemical Reagents

The generation and specificity of the rabbit polyclonal antibodies to ICP10, which recognizes an epitope that is retained by both ICP10 and the PK deleted ICP10 protein p95 and H11/HspB832 were previously described (22. Perkins D, Pereira E F, Aurelian L. The herpes simplex virus type 2 R1 protein kinase (ICP10 PK) functions as a dominant regulator of apoptosis in hippocampal neurons involving activation of the ERK survival pathway and upregulation of the antiapoptotic protein Bag-1. *J Virol* 2003; 77: 1292-1305; Laing J M, Gober M D, Golembewski E K, Thompson S M, Gyure K A, Yarowsky P J, et al. Intranasal administration of the growth-compromised HSV-2 vector DeltaRR prevents kainate-induced seizures and neuronal loss in rats and mice. *Mol Ther* 2006; 13: 870-881. Erratum in: Mol Ther. 2007 September; 15 (9):1734; Gober M D, Laing J M, Thompson S M, Aurelian L. The growth compromised HSV-2 mutant DeltaRR prevents kainic acid-induced apoptosis and loss of function in organotypic hippocampal cultures. *Brain Res* 2006; 1119: 26-39; Golembewski E K, Wales S Q, Aurelian L, Yarowsky P J. The HSV-2 protein ICP10PK prevents neuronal apoptosis and loss of function in an in vivo model of neurodegeneration associated with glutamate excitotoxicity. *Exp Neurol* 2007; 203: 381-393; Wales S Q, Li B, Laing J M, Aurelian L. The herpes simplex virus type 2 gene ICP10PK protects from apoptosis caused by nerve growth factor deprivation through inhibition of caspase-3 activation and XIAP up-regulation. *J Neurochem* 2007; 103: 365-379; Wales S Q, Laing J M, Chen L, Aurelian L. ICP10PK inhibits calpain-dependent release of apoptosis-inducing factor and programmed cell death in response to the toxin MPP+. *Gene Ther* 2008; 15: 1397-1409; Smith C C, Peng T, Kulka M, Aurelian L. The PK domain of the large subunit of herpes simplex virus type 2 ribonucleotide reductase (ICP10) is required for immediate-early gene expression and virus growth. *J Virol* 1998; 72: 9131-9141; Smith C C, Nelson J, Aurelian L, Gober M, Goswami B B. Ras-GAP binding and phosphorylation by herpes simplex virus type 2 RR1 PK (ICP10) and activation of the Ras/MEK/MAPK mitogenic pathway are required for timely onset of virus growth. *J Virol* 2000; 74: 10417-10429).

The following antibodies were purchased and used according to manufacturer's instructions. Antibodies to caspase-3 (recognizes both the zymogen and its cleavage products), activated caspase-3 (caspase-3 p20), activated human caspase-1, calpain (p80, p78, p28), Beclin-1, ERK½, and actin were purchased from Santa Cruz Biotechnology (Santa Cruz, Calif.). Antibodies to activated caspase-7, phosphorylated (activated) Akt (pAkt), and total Akt were purchased from Cell Signaling Technology (Danvers, Mass.), antibody to phosphorylated (activated) ERK ½ (pERK½) from Promega (Madison, Wis.), antibody to CD11b (Mac-lm chain-biotin conjugated) from Leinco (St. Louis, Mo.), antibody to the HSV major capsid protein VP5 from Virusys Corporation (Sykesville, Md.), and antibody to TNF-alpha from R&D Systems (Minneapolis, Minn.). Alexafluor 594-conjugated anti-mouse and Alexafluor 488-conjugated anti-rabbit secondary antibodies were purchased from Invitrogen (Carlsbad, Calif.). HRP-conjugated anti-rabbit and anti-mouse antibodies were purchased from Cell Signalling Technologies (Danvers, Mass.). The in situ cell death detection kit (TUNEL) with Fluorescein (FITC) labeled dUTP was purchased from Roche (Indianapolis, Ind.), the calpain inhibitor PD150606 from Calbiochem (La Jolla, Calif.), and the pan-caspase inhibitor benzyloxcarbonyl-Val-Ala-Asp-fluormethyl ketone (z-VAD-fmk) from Sigma-Aldrich (St. Louis, Mo.) and Promega.

Example 4

Virus Growth

To measure virus replication in culture, cells were infected at a multiplicity of infection (moi) of 0.5 pfu/cell. Adsorption was for 1 hr at 4 degrees C. (synchronized infection). At this time, virus was removed and cells were overlaid with MEM with 0% or 10% FBS [0 hrs post-infection (p.i.)]. They were collected at various times p.i. and virus was released by 7 freeze-thaw cycles and sonication [60 seconds at 25% output power using a Sonicator/Ultrasonic processor (Misonix, Inc., Farmingdale, N.Y.]). Virus titers were determined by plaque assay on Vero cells and the results are expressed as mean pfu/cell (burst size), as described (Li B, Smith C C, Laing J M, Gober M D, Liu L, Aurelian L. Overload of the heat-shock protein H11/HspB8 triggers melanoma cell apoptosis through activation of transforming growth factor-beta-activated kinase 1. *Oncogene* 2007; 26: 3521-3531). To determine the titers of infectious virus in delta-PK treated xenografts, tissues (15 mg samples) collected at 7 days after the last injection were suspended in 50 .mu.l of virus adsorption medium (PBS supplemented with 0.2% glucose and 0.2% BSA) and homogenized on ice using a sterile pre-chilled micro-pestle. The homogenates were cleared of cell debris by centrifugation (3,000×g, 10 min, 4.degree.C.) and virus titers were determined by plaque assay.

Example 5

Immunoflourescence and Immunohistochemistry

For immunofluorescence, cells grown on glass coverslips, were fixed with 4% paraformaldehyde overnight at 4 C. Cells were then blocked with 5% normal goat serum and 5% BSA (30 min. at room temperature) and incubated with primary antibody overnight at 4.degree.C. Cells were washed in PBS with 0.1% Tween 20, exposed to fluorochrome-labeled secondary antibodies (37 C., 1 hr) and mounted in Vectashield with DAPI (Vector Laboratories, Burlingame, Calif., USA). Slides were visualized with an Olympus BX50 fluorescence microscope utilizing UV (for DAPI) (330-380 nm), FITC (465-495nm), and Texas red (540-580 nm) cubes. Stained cells were counted in five randomly selected 3 mm$^2$ fields (>250 cells each) and the percentage of positive cells was calculated relative to total number of cells imaged by DAPI, as previously described (Laing J M, Gober M D, Golembewski E K, Thompson S M, Gyure K A, Yarowsky P J, et al. Intranasal administration of the growth-compromised HSV-2 vector DeltaRR prevents kainate-induced seizures and neuronal loss in rats and mice. Mol Ther 2006; 13: 870-881. Erratum in: Mol Ther. 2007 September; 15(9):1734; Gober M D, Laing J M, Thompson S M, Aurelian L. The growth compromised HSV-2 mutant DeltaRR prevents kainic acid-induced apoptosis and loss of function in organotypic hippocampal cultures. Brain Res 2006; 1119: 26-39; Golembewski E K, Wales S Q, Aurelian L, Yarowsky P J. The HSV-2 protein ICP10PK prevents neuronal apoptosis and loss of function in an in vivo model of neurodegeneration associated with glutamate excitotoxicity. Exp Neurol 2007; 203: 381-393; Wales S Q, Li B, Laing J M, Aurelian L. The herpes simplex virus type 2 gene ICP10PK protects from apoptosis caused by nerve growth factor deprivation through inhibition of caspase-3 activation and XIAP up-regulation. J Neurochem 2007; 103: 365-379; Wales S Q, Laing J M, Chen L, Aurelian L. ICP10PK inhibits calpain-dependent release of apoptosis-inducing factor and programmed cell death in response to the toxin MPP+. Gene Ther 2008; 15: 1397-1409).

For immunohistochemistry, tumor sections were post fixed (30 min.) in 4% paraformaldehyde in PBS (w/v), treated (10 min) with 0.3% H2O2 to remove endogenous peroxidases, permeabilized and blocked in blocking solution (10% goat serum, 1% BSA, and 0.3% Triton-X 100 in PBS) for 1 hr. Sections (20 µm) were exposed overnight (4 degrees C.) to the primary antibody diluted in blocking solution followed by HRP-conjugated secondary antibody diluted in 5% goat serum and 5% BSA (1 hr). The reaction was developed with IMMPACT DAB substrate (Vector Laboratories, Burlingame, Calif.) and the sections were counterstained with Mayer's Hematoxylin (Sigma-Aldrich). They were dehydrated and mounted in Permount (Sigma-Aldrich). Visualization was with an Olympus BX50 microscope under brightfield conditions. Stained cells were counted in representative 50 µm$^2$ fields in each of 4 tumors/treatment and the percentage of positive cells was calculated relative to the total cells/field, as described (Laing J M, Gober M D, Golembewski E K, Thompson S M, Gyure K A, Yarowsky P J, et al. Intranasal administration of the growth-compromised HSV-2 vector DeltaRR prevents kainate-induced seizures and neuronal loss in rats and mice. Mol Ther 2006; 13: 870-881. Erratum in: Mol Ther. 2007 September; 15 (9):1734; Gober M D, Laing J M, Thompson S M, Aurelian L. The growth compromised HSV-2 mutant DeltaRR prevents kainic acid-induced apoptosis and loss of function in organotypic hippocampal cultures. Brain Res 2006; 1119: 26-39; Golembewski E K, Wales S Q, Aurelian L, Yarowsky P J. The HSV-2 protein ICP10PK prevents neuronal apoptosis and loss of function in an in vivo model of neurodegeneration associated with glutamate excitotoxicity. Exp Neurol 2007; 203: 381-393; Wales S Q, Li B, Laing J M, Aurelian L. The herpes simplex virus type 2 gene ICP10PK protects from apoptosis caused by nerve growth factor deprivation through inhibition of caspase-3 activation and XIAP up-regulation. J Neurochem 2007; 103: 365-379; Wales S Q, Laing J M, Chen L, Aurelian L. ICP10PK inhibits calpain-dependent release of apoptosis-inducing factor and programmed cell death in response to the toxin MPP+. Gene Ther 2008; 15: 1397-1409; Smith C C, Nelson J, Aurelian L, Gober M, Goswami B B. Ras-GAP binding and phosphorylation by herpes simplex virus type 2 RR1 PK (ICP10) and activation of the Ras/MEK/MAPK mitogenic pathway are required for timely onset of virus growth. J Virol 2000; 74: 10417-10429; Laing J M, Aurelian L. DeltaRR vaccination protects from KA-induced seizures and neuronal loss through ICP10PK-mediated modulation of the neuronal-microglial axis. Genet Vaccines Ther 2008; 6: 1).

Example 6

Cell Death and TUNEL Staining

Cell death was determined by trypan blue exclusion and staining with ethidium homodimer-1 (EtHD), a cell impermeable red fluorescent nuclear stain that increases intensity after binding to the DNA of dead cells. For trypan blue staining, cells were collected by centrifugation and the pellet was resuspended in 50 µl PBS to which 50 µl trypan blue was added. Dead cells were counted by four independent hemacytometer counts. EtHD staining was done as per manufacturer's instructions and visualized by microscopy at 4× magnification using a Nikon E4100 fluorescent microscope utilizing phase contrast and a Texas Red (540-580 nm) cube. Stained cells were counted in five randomly selected 3 mm$^2$ fields (≧250 cells each), and the % positive cells was calculated relative to total number of cells imaged by phase contrast microscopy (Gober M D, Laing J M, Thompson S M, Aurelian L. The growth compromised HSV-2 mutant DeltaRR prevents kainic acid-induced apoptosis and loss of function in organotypic hippocampal cultures. Brain Res 2006; 1119: 26-39). Detection of apoptotic DNA fragmentation with 3'-OH ends by the terminal deoxynucleotidyl transferase-mediated dUTP nick end labeling (TUNEL) assay used the in situ cell death detection kit (Roche) as per manufacturer's instructions.

Example 7

Immunoblotting

Cultured cells were lysed with radioimmunoprecipitation buffer [RIPA; 20 mM Tris-HCl (pH 7.4), 0.15 mM NaCl, 1% Nonidet P-40, 0.1% sodium dodecyl sulfate (SDS), 0.5% sodium deoxycholate] supplemented with protease and phosphatase inhibitor cocktails (Sigma-Aldrich), and sonicated twice for 30 seconds at 25% output power with a sonicator ultrasonic processor (Misonix, Inc., Farmingdale, N.Y.).

Xenograft tissues were weighed, resuspended in RIPA buffer (0.5 ml/g), homogenized using a pre-chilled motorized pestle (Kontes, Vineland N.J.), and cleared of cell debris by centrifugation (10,000×g; 4 degrees C. for 30 min.). Protein concentration was determined by the bicinchoninic assay (Pierce, Rockford, Ill.), and 100 µg protein samples were resolved by SDS-polyacrylamide gel elecrophoresis (SDS-PAGE) and transferred to polyvinylidene fluoride membranes followed by immunoblotting. Immunoblotting was performed by standard techniques. Briefly, membranes were blocked (1 hr, room temperature) in 5% nonfat milk in TN-T buffer (0.01 M Tris-HCl pH 7.4, 0.15 M NaCl, 0.05% Tween-20), exposed (1 hr) to primary antibodies, washed in TN-T buffer, and incubated (1 hr) in HRP-conjugated secondary antibodies. Detection was with ECL reagents (Amersham, Pittsburg, Pa.) and high performance chemiluminescence film (Hyperfilm ECL, Amersham). Quantitation was by densitometric scanning with the Bio-Rad GS-700 imaging densitometer (Bio-Rad, Hercules, Calif.). The results are expressed as the mean actin-adjusted densitometric units +/−SD.

Example 8

Delta-PK Tumor Selective Growth

Figure 2A:
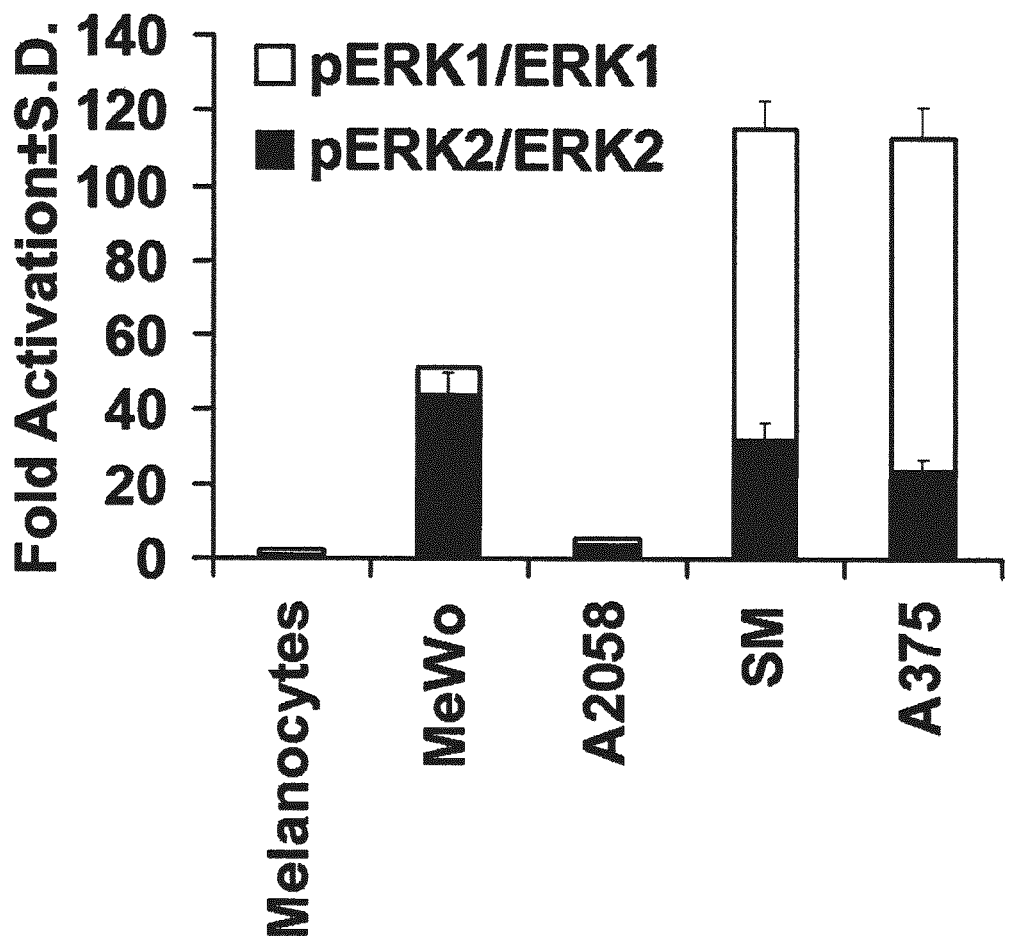
FIG. 2. Melanoma cultures have distinct ERK/Akt activation patterns. A. Extracts of melanocytes and representative melanoma cultures MeWo, A2058, SM, and A375 were immunoblotted with antibodies to pERK½ and total ERK½. B. Extracts of melanocytes and representative melanoma cultures MeWo, A2058, SM, and A375 were immunoblotted with antibodies to pAKT and total AKT. Data were quantified by densitometry. pERK/ERK and pAKT/AKT ratios were calculated and the results expressed as fold activation +/−S.D. relative to melanocytes.
Figure 2B:
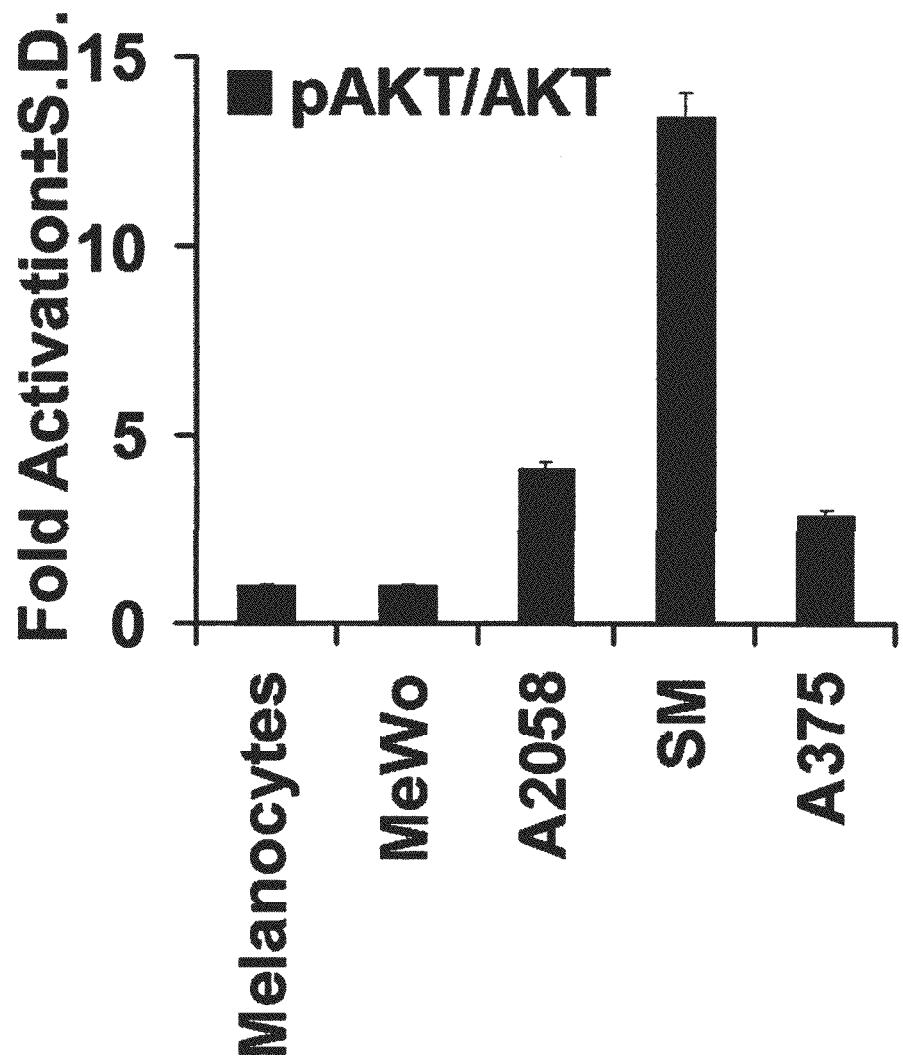
Figure 3B:
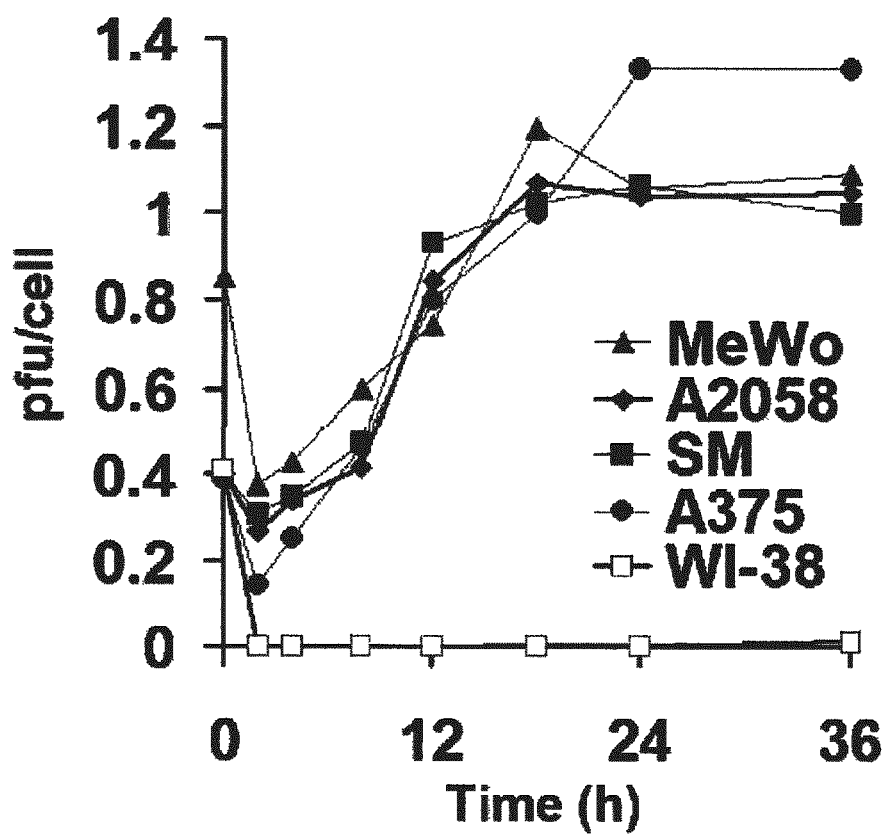
FIG. 3. Delta-PK is a growth-restricted replication competent oncolytic virus. A. Vero cells were infected with HSV-2, delta-PK, or HSV-2(R) (moi=0.5) in serum-free medium and virus titers were determined by plaque assay. Results are expressed as mean pfu/cell (burst size). B. A2058, MeWo, SM, A375 and Wi-38 cells were infected with delta PK and examined for virus growth. Similar growth patterns were seen in melanoma cultures LM, SK-MEL-2, LN, OV and BUL. Delta-PK did not grow in WI-38 cells and in normal melanocytes, but HSV-2 and HSV-2(R) replicated equally well in all the cultures. C. Delta-PK infected A2058 and WI-38, cells were stained with Alexafluor-488 labeled ICP10 and Alexafluor-594 labeled VP5 antibodies in double immunofluorescence. Cells were counted in 3 randomly selected fields ($\geq$250 cells) and the % staining cells calculated relative to total cells identified by DAPI staining. Quantitative results are shown for A2058 cell at 4-72 hrs p.i., and for WI-38 cells at 48 hrs p.i. Similar results were obtained for the partially purified virus.
Figure 3C:
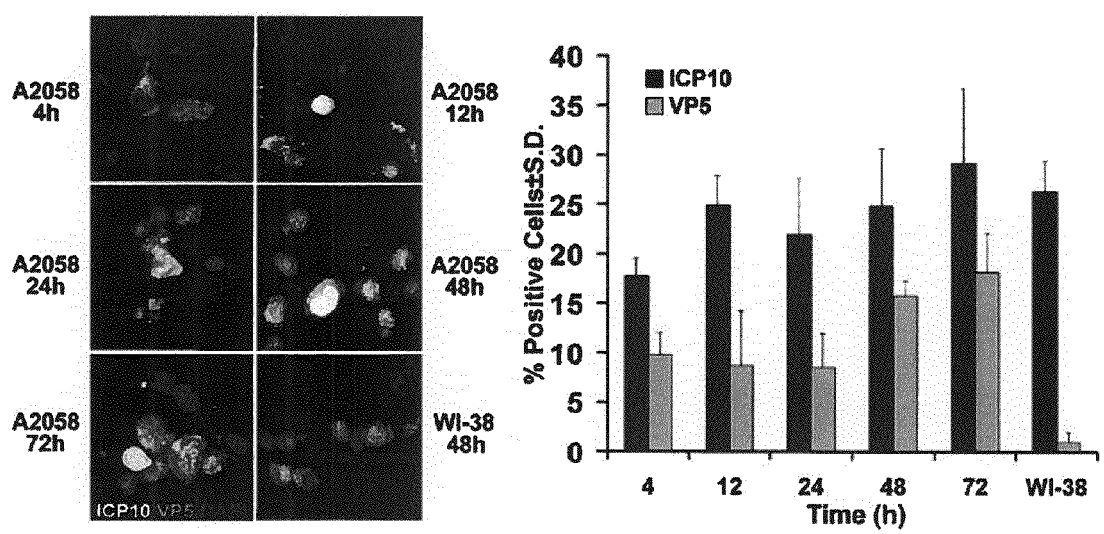

Delta-PK is growth restricted in Vero (African green monkey kidney) cells cultured in low serum, a property associated with its failure to activate Ras signaling pathways (33, 34). Because the Ras and B-Raf pathways are activated in most melanoma cultures, the inventors explored whether this compensates for virus growth, providing conditions that enable the tumor selectivity characteristic of oncolytic viruses. A panel of 9 human melanoma cultures were, which included established (A2058, A375, SKMEL-2, MeWo) and freshly prepared lines (LM, SM, LN, OV, BUL) with different patterns of activated ERK and/or Akt (FIG. 2). Controls were Vero cells, which grow in agarose and cause tumors in animals, at least at a relatively high passage and normal human lung fibroblasts (WI-38) and melanocytes, both of which are primary growth-limited cultures (Manohar M, Orrison B, Peden K, Lewis A M, Jr. Assessing the tumorigenic phenotype of VERO cells in adult and newborn nude mice. *Biologicals* 2008; 36: 65-72). The cells were infected with delta-PK (moi=0.5) and assayed for virus growth by plaque assay. Consistent with previous findings, the growth of HSV-2 and the revertant virus HSV-2(R) began at 4 hrs p.i. and reached a maximal burst size (976+/−12 pfu/cell) at 24 hrs p.i. (Smith C C, Peng T, Kulka M, Aurelian L. The PK domain of the large subunit of herpes simplex virus type 2 ribonucleotide reductase (ICP10) is required for immediate-early gene expression and virus growth. *J Virol* 1998; 72: 9131-9141; Smith C C, Nelson J, Aurelian L, Gober M, Goswami B B. Ras-GAP binding and phosphorylation by herpes simplex virus type 2 RR1 PK (ICP10) and activation of the Ras/MEK/MAPK mitogenic pathway are required for timely onset of virus growth. *J Virol* 2000; 74: 10417-10429). By contrast, the growth of delta-PK began at 12 hrs p.i. and reached maximal, albeit low, levels (1.1+/−0.1 pfu/cell) at 36 hrs p.i. (FIG. 3A). This temporal restriction was released in melanoma cultures, as shown for A2058, MeWo, SM and A375 cells, with growth beginning at 4 hrs p.i. as determined both by the burst size (pfu/cell) (FIG. 3B) and staining with antibody to the major capsid protein VP5 (FIG. 3C). However, the maximal yields of infectious virus (1.1+/−0.2 pfu/cell), seen at 18-24 hrs p.i. were similar to those seen in Vero cells (FIG. 3B). The number of VP5+ cells was also relatively low (16+/−1% at 48 hrs p.i.) and similar results were obtained for melanoma cultures LM, SKMEL-2, LN, QV and BUL. This was unrelated to the ability of delta-PK to infect the cells, because the % cells staining with ICP10 antibody (recognizes the PK deleted ICP10 protein, also known as p95), which is regulated with IE kinetics and is expressed in the absence of VP5 was consistent with the rate of infection for the studied moi (25+/−5% as early as 4 hrs p.i.) (FIG. 3C). Delta-PK did not grow in WI-38 cells (FIG. 3B), but there was a similar % of cells staining with ICP10 antibody (27+/−3%; FIG. 3C), indicative of infection. Normal melanocytes behaved like WI-38 cells. These findings are in contrast to those obtained for HSV-2 and HSV-2 (R), the growth of which was similar to that seen in Vero cells for all the studied cultures (921+/−54 and 737+/−28 pfu/cell, respectively at 24 hrs). Collectively, the data indicate that delta-PK has selective growth potential for transformed/tumor cells.

Example 9

Figure 4A:
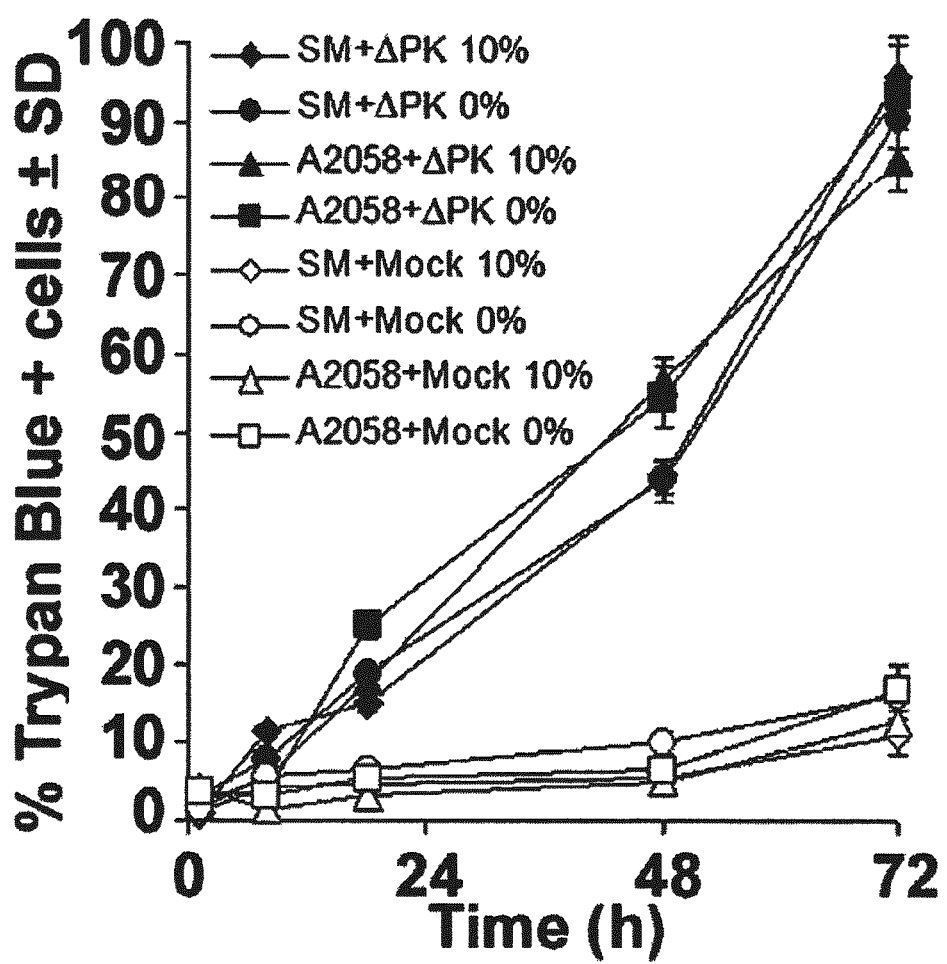
FIG. 4. Delta-PK mediated melanoma oncolysis includes a robust PCD bystander component. A. A2058 and SM melanoma cultures infected with delta-PK (moi=0.5) or mock infected with adsorption medium were cultured in medium without (0%) or with (10%) FBS and cells were stained with trypan blue at various times p.i. Four independent haemacytometer counts were performed and % staining cells was calculated. Results from 3 replicate experiments are expressed as mean % staining cells. B. Melanoma, primary normal melanocytes, and normal fibroblasts (WI-38) infected and cultured in serum-free medium were stained with EtHD. Cells were counted in 3 randomly selected fields ($\geq$250 cells) and the % staining cells calculated.
Figure 5:
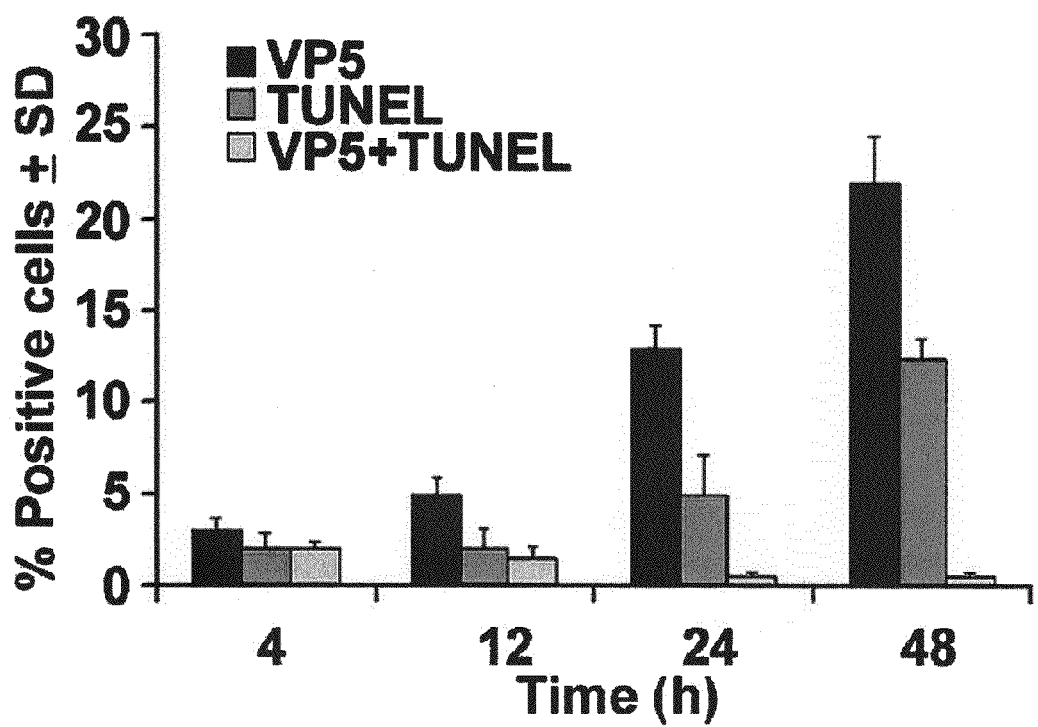
FIG. 5. Apoptosis is a small component of the delta-PK induced bystander effect. A2058 cells were infected with delta-PK (moi=0.5). At 4-48 hrs p.i., cells were stained with Alexafluor 594-labeled VP5 antibody (reflects virus replication) and examined for cell death using the in situ cell death detection kit (Roche) that employs FITC-labeled dUTP according to the manufacturer's instructions. Cells were counted in five randomly selected fields ($\geq$250 cells), and the % positive cells calculated relative to total cells identified by DAPI staining. Results are expressed as % VP5+ and TUNEL+ (apoptotic) cells +/−S.D.

Delta-PK Induced Melanoma Oncolysis Includes a Robust Component Other than Viral Replication Delta-PK infected melanoma cultures were examined for cell death by morphology [cytopathogenic effect (CPE)], trypan blue exclusion, and EtHD staining at 0-72 hrs p.i. Cultures mock-infected with PBS and delta-PK infected freshly isolated normal melanocytes and WI-38 cells were studied in parallel and served as controls. Delta-PK caused a time-dependent increase in CPE in all the melanoma cultures, with virtually all cells becoming rounded, refractile and detached by 72 hrs p.i. This was accompanied by increased staining with trypan blue (85-95% positive cells at 72 hrs p.i.) or EtHD (63-85% positive cells at 72 hrs p.i.) and similar results were obtained for cultures grown in serum-free medium or in medium supplemented with 10% FBS (FIGS. 4 A and B). Duplicate cultures obtained at the same times were stained with antibody to VP5 and the % dead cells (trypan blue and/or EtHD+) was evaluated relative to the % of VP5 staining cells. The ratio of trypan blue+ or EtHD+/VP5+ cells ranged between 1.8-4.1 for the different cultures at 24-72 hrs p.i, with an average of 2.8, suggesting that a major component of cell death is through a program other than lysis caused by productive virus replication (bystander effect). In this context it is important to point out that VP5 also did not co-localize with TUNEL, a marker of canonical apoptosis, which was a relatively minor component (12.4+/−1.1% cells at 48 hrs p.i) of the delta-PK bystander effect (FIG. 5). Delta-PK-infected primary melanocytes and WI-38 cells did not stain with trypan blue or EtHD (3.4-5.7% positive cells throughout the study interval), supporting the conclusion that delta-PK induced cell death is selective for cancer/transformed cells. Similar results were obtained with virus purified as previously described (Sheridan J F, Beck M, Smith C C, Aurelian L. Reactivation of herpes simplex virus is associated with production of a low molecular weight factor that inhibits lymphokine activity in vitro. *J Immunol* 1987; 138: 1234-1239).

Example 10

Calpain and Caspases-7 and -3 Activation by Delta-PK

Figure 6A:
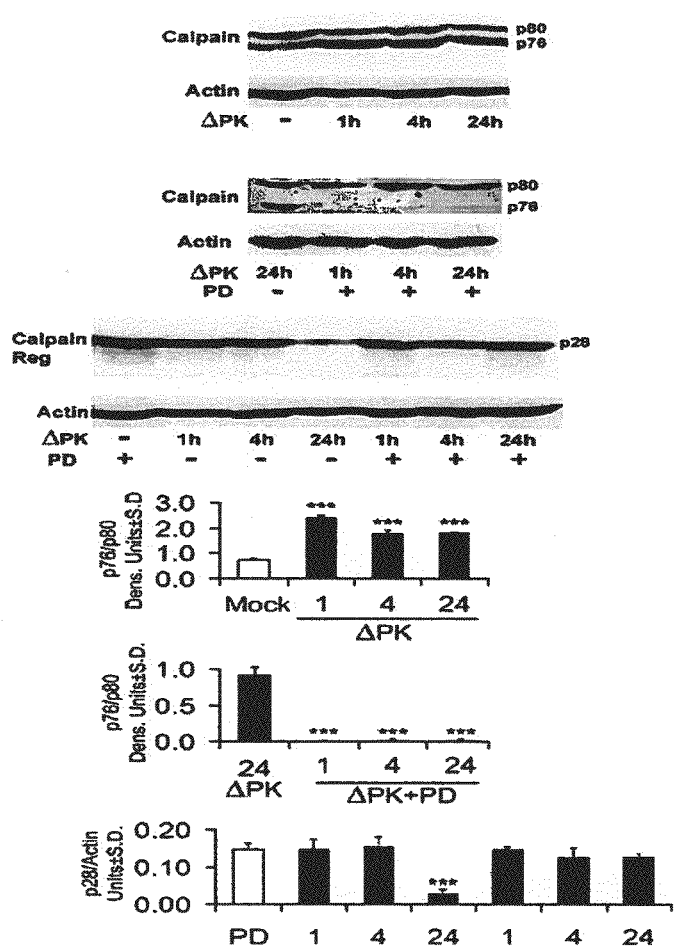
FIG. 6. Calpain and caspase-7 and caspace-3 are activated in delta-PK infected melanoma cells. A. A2058 cells were infected with delta-PK (moi=0.5) or mock infected with PBS in the absence or presence of the calpain inhibitor PD150606 (100 µM) and cell extracts obtained at various times p.i. were immunoblotted with antibody to calpain that recognizes the inactive (p80), activated (p76), and regulatory (p28) species. Data were quantified by densitometry and expressed as the ratio of the p76/p80 and p28 densitometric units +/−SD, respectively. Representatives of three replicate experiments are shown (*$p<0.001$ vs. Mock). B. The immunoblots in FIG. 6A were sequentially stripped and re-probed with antibodies to activated caspase-7, activated caspase-3, and actin. Data were quantified by densitometry and results are expressed as densitometric units +/−SD ($p<0.01$, *$p<0.001$ vs. Mock). C. Extracts of A2058 melanoma cells infected with delat-PK (moi=0.5) with or without z-VAD-fmk (Sigma-Aldrich, 100 muM or Promega, 20 .mu.M) and cell extracts obtained at 24 h p.i. were immunoblotted with antibody to activated caspase-7. Representatives of three replicate experiments are shown (*$p<0.001$ vs. delta-PK alone).
Figure 6B:
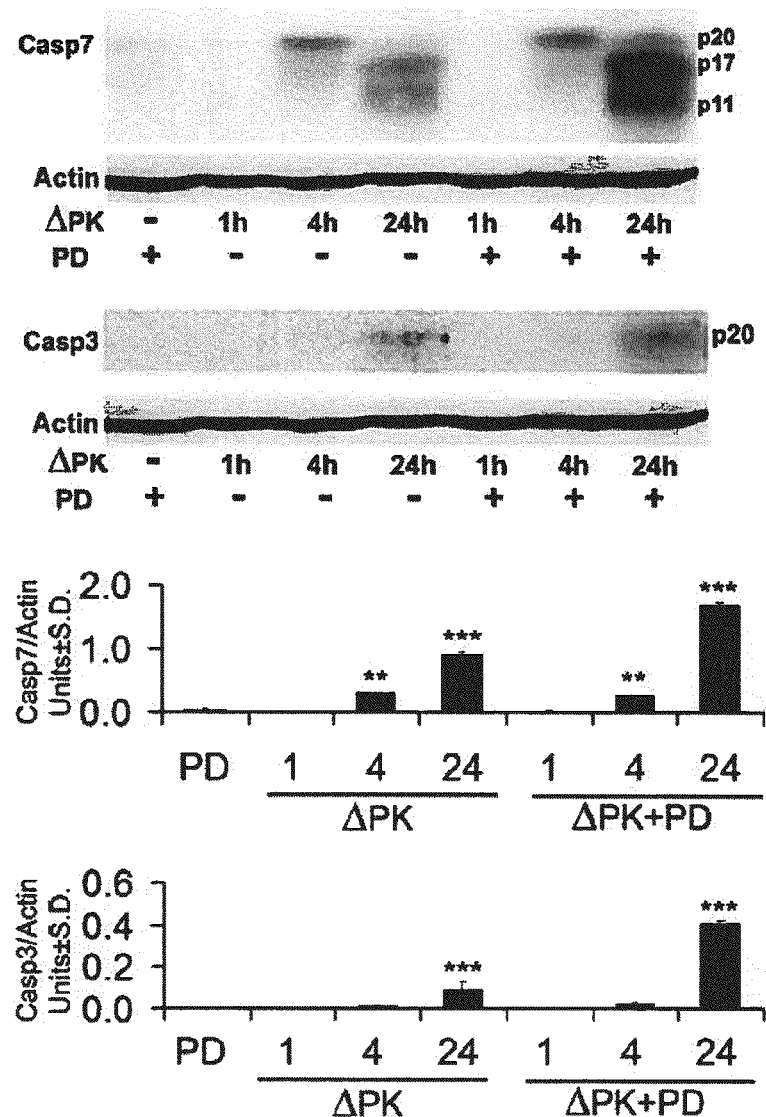

Extracts of melanoma cells infected with delta-PK for 0-24 hrs were immunoblotted with antibodies to calpain, and caspase-7 and caspase-3 and the results were quantitated by densitometric scanning. As shown for A2058 cells, delta-PK caused sequential and apparently independent activation of these three proteases. Calpain, activation, expressed as an increased ratio of the active (p76) to inactive (p80) forms of the catalytic subunit, was first seen at 1 hr p.i. and it was followed at 24 hrs p.i. by the loss of the p28 regulatory subunit (FIG. 6A), which is another marker of enzyme activation (Goll D E, Thompson V F, Li H, Wei W, Cong J. The calpain system. *Physiol Rev* 2003; 83: 731-801). Activation of caspase-7 was first seen at 4 hrs p.i, as evidenced by the appearance of the caspase-7p20 cleavage product and it continued with time p.i., with the smaller p17 and p11 breakdown products seen at 24 hrs p.i. (FIG. 6B). Activation of caspase-3 was first seen at 24 hrs p.i., and it appeared to be less robust than that seen for caspase-7, as determined by the levels of the respective cleavage products (FIG. 6B).

Figure 6C:
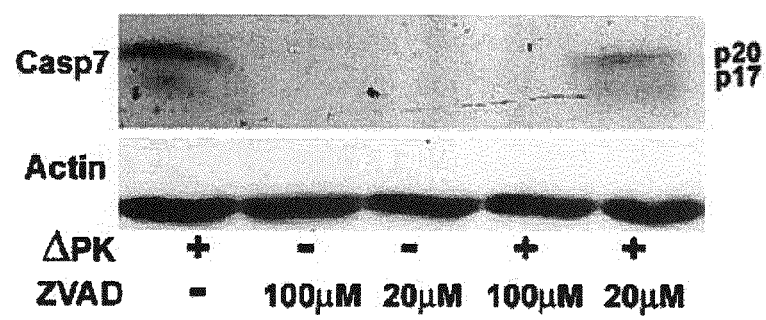
Figure 6C:
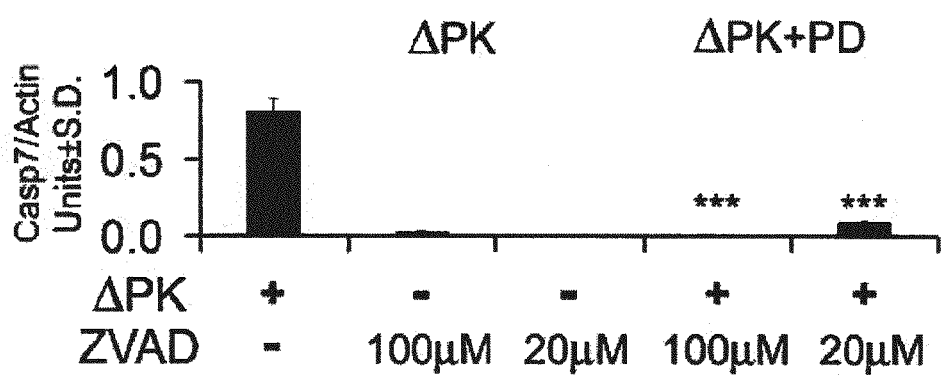

Because calpain can attenuate or facilitate the activity of the caspases and it is activated before them under the conditions of these experiments, the inventors explored whether calpain activation contributes to the ability of delta-PK to activate these caspases. Extracts from duplicate cultures infected with delta-PK in the absence or presence of the calpain inhibitor PD150606 (100 .mu.M) were immunoblotted with antibodies to calpain followed by caspase-7 and caspase-3. Calpain activation was inhibited by PD150606, as evidenced by reduced p76/p80 ratios and retention of p28 (FIG. 6A). By contrast, the levels of the caspase cleavage products (caspase-7p17 and p11 and caspase-3p17) were increased, at least at 24 hrs p.i. (FIG. 6B). This is not a technical artifact, because caspase activation was inhibited by the pan-caspase inhibitor z-VAD-fmk (100 .mu.M, Sigma-Aldrich; 20 .mu.M Promega), as shown for caspase-7 (FIG. 6C). z-VAD-fmk did not affect calpain activation, and neither PD150606, nor z-VAD-fmk had any effect on virus growth. Similar results were obtained for all the studied melanoma cultures, both in terms of protease activation and its inhibition. Collectively, the data indicate that calpain reduces, but does not abrogate the ability of delta-PK to cause caspase activation, supporting that these are independent events.

Example 11

Delta-PK Induced Oncolysis is Calpain and Caspase Dependent

Figure 7A:
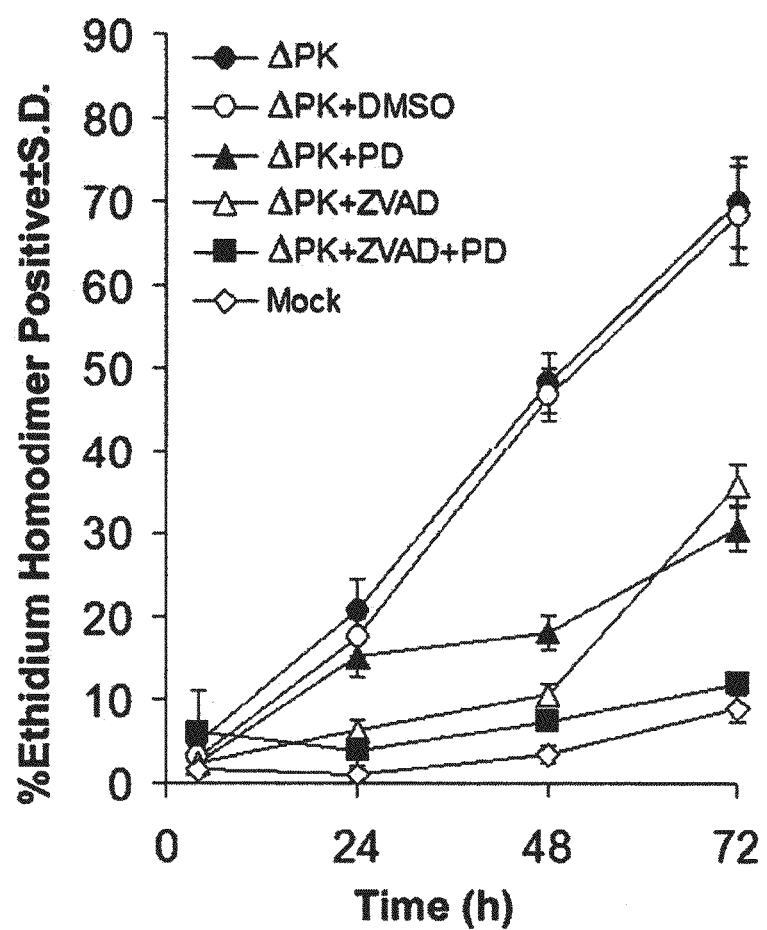
FIG. 7. Delta-PK induced melanoma cell death is both calpain and caspase-dependent. A. A2058 cells were infected with delta-PK (moi=0.5) or mock-infected with PBS and cultured without or with PD150606 (100 µM), z-VAD-fmk (20 .mu.M) or both PD150606 and z-VAD-fmk. DMSO (28 mM) was used as vehicle control. Replicate cultures (n=3) were stained with EtHD at various times p.i. and the % staining cells calculated. B. A375 cells were infected with delta-PK (moi=0.5) in the absence or presence of inhibitors and stained with EtHD+. Delta-PK infected WI-38 cells and mock infected DMSO treated cells served as controls.
Figure 7B:
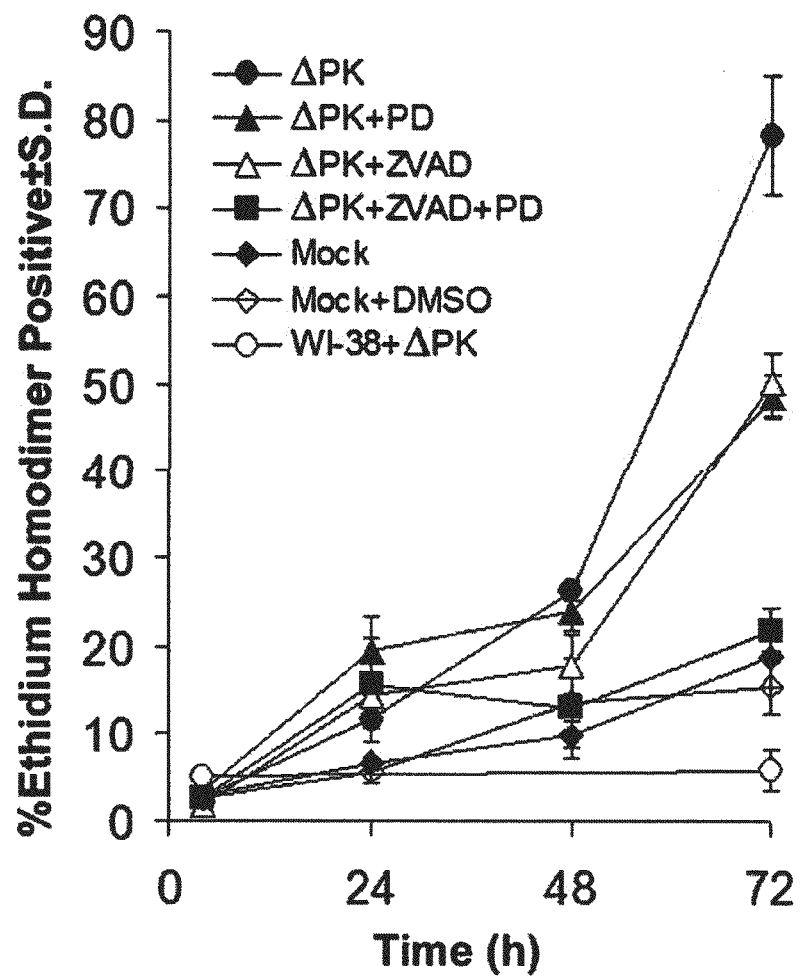

To examine the role of the activated proteases in delta-PK induced melanoma cell death, cultures were mock infected with PBS or infected with delta-PK in the absence or presence of PD150606 or/and z-VAD-fmk and cell death was determined at 0-72 hrs p.i. by EtHD staining. As shown in FIG. 7A for A2058 and A375 cells, delta-PK caused a time-dependent increase in the % EtHD+ cells that reached maximal levels at 72 hrs p.i. (70.1+/−5.4% and 78.4+/−6.8%, respectively). This percentage was significantly decreased by PD150606 (30.7+/−2.8% and 49.1+/−2.5% for A2058 and A375 cells, respectively) or z-VAD-fmk (35.8+/−2.5% and 49.6+/−3.7% for A2058 and A375 cells, respectively), but cell death was abrogated in cells treated with the combination of both inhibitors. The data indicate that calpain and caspase activation contribute to delta-PK induced melanoma oncolysis, supporting the conclusion that the two death pathways function independently.

Example 12

In Vivo Cell Killing of Delta-PK

Figure 8A:
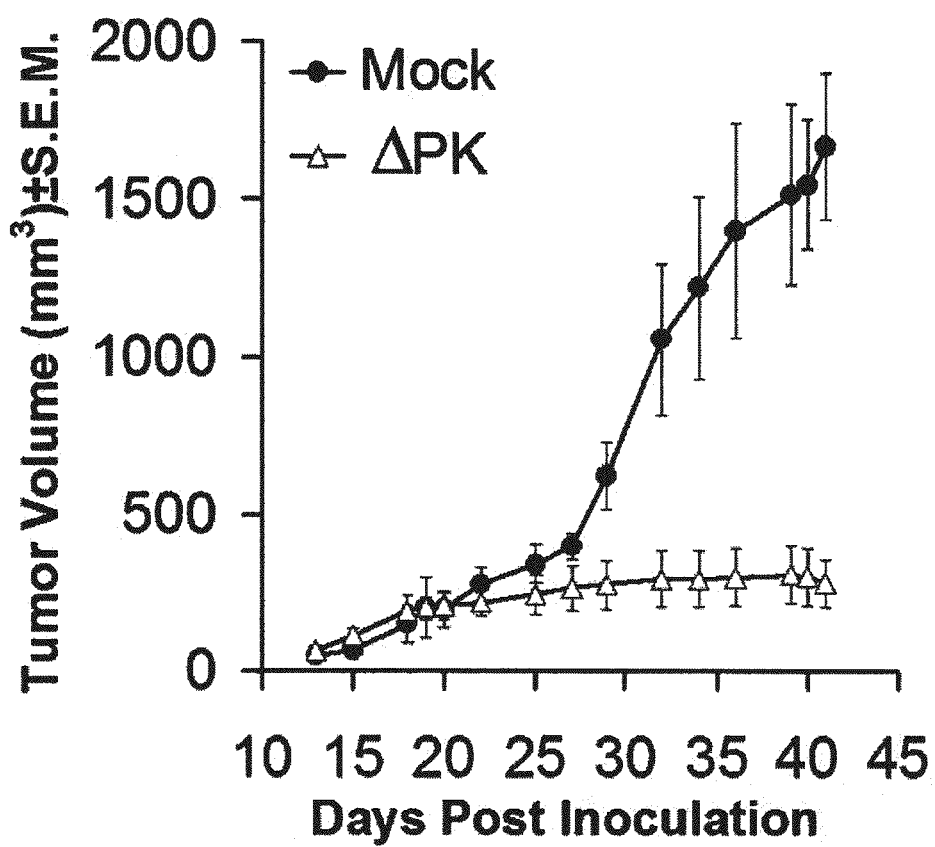
FIG. 8. Delta-PK inhibits the growth of melanoma xenografts. A. A2058 melanoma cells ($10^7$) were implanted subcutaneously into both flanks of Balb/c nude mice and given intra-tumoral (i.t.) injections (100 .mu.l) of delta-PK (n=12; $10^7$ pfu) or growth medium (n=6; mock) beginning on day 14, when the tumors were palpable (approximately 200 $mm^3$). The difference between mock and delta-PK treated animals became statistically significant on day 32 ($p<0.001$ by 2-way ANOVA) and remained significant to the end of the study. Representative animals and tumor tissues were photographed at day 42. B. A375 xenografts were established and tested. The difference between mock and delta-PK treatment became statistically significant at day 23 and remained significant by the end of the study ($p<0.001$ by 2-way ANOVA). C. LM melanoma cells ($10^7$) were implanted subcutaneously into both flanks of Balb/c nude mice and given 4 i.t. injections of delta-PK (n=6; $10^6$ pfu) or growth medium (n=6; mock) at weekly intervals beginning on day 7, when the tumors were palpable. Tumor volume in 4 animals was monitored for 5 months after the last delta-PK injection. The difference between mock and delta-PK treatment became statistically significant on day 14 ($p<0.001$ by 2-way ANOVA) and remained significant to the end of the study. Three delta-PK treated mice showing complete tumor eradication were photographed at day 35. D. Kaplan-Meier survival analysis in animals given LM xenografts with the terminal event set at 1.5 cm diameter of growth in any one direction. Survival of delta-PK treated mice was significantly reduced when compared to mock treated (p<0.001) by Log Rank (Mantel-Cox) analysis.
Figure 8B:
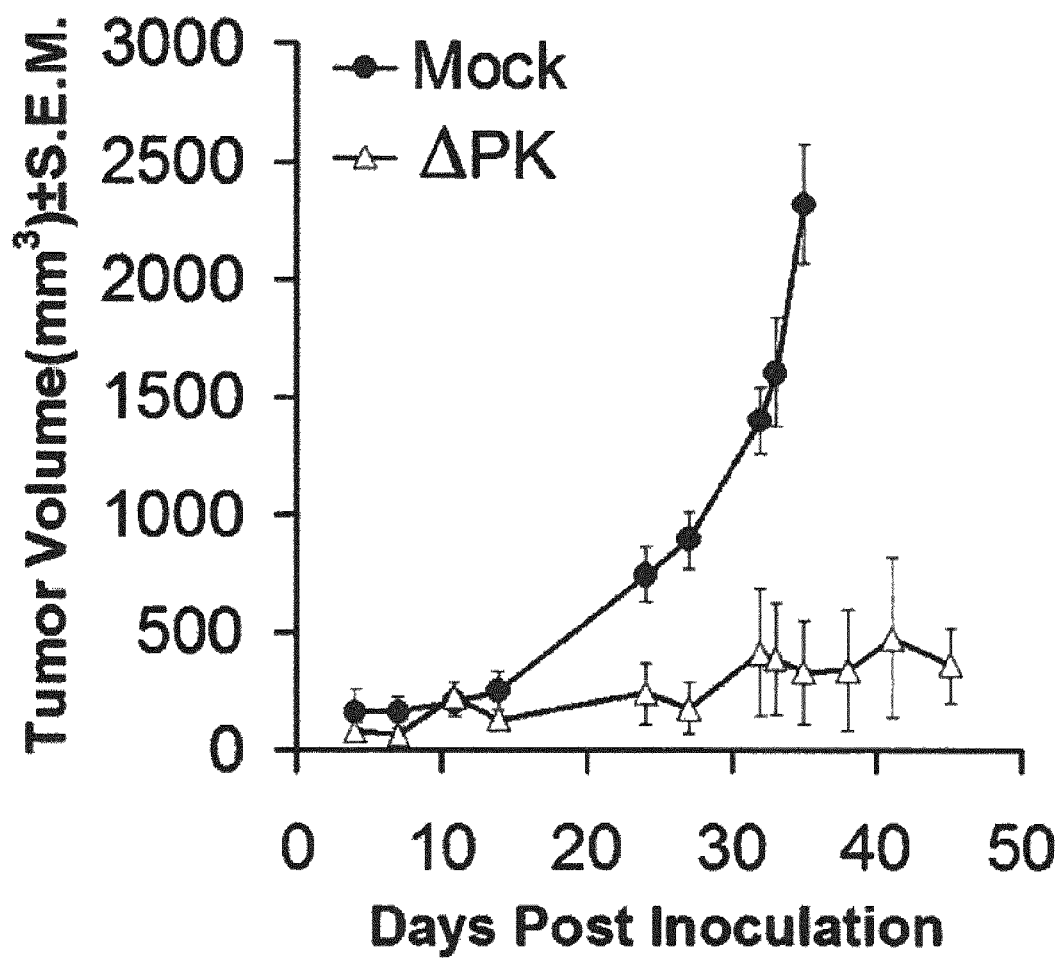
Figure 8C:
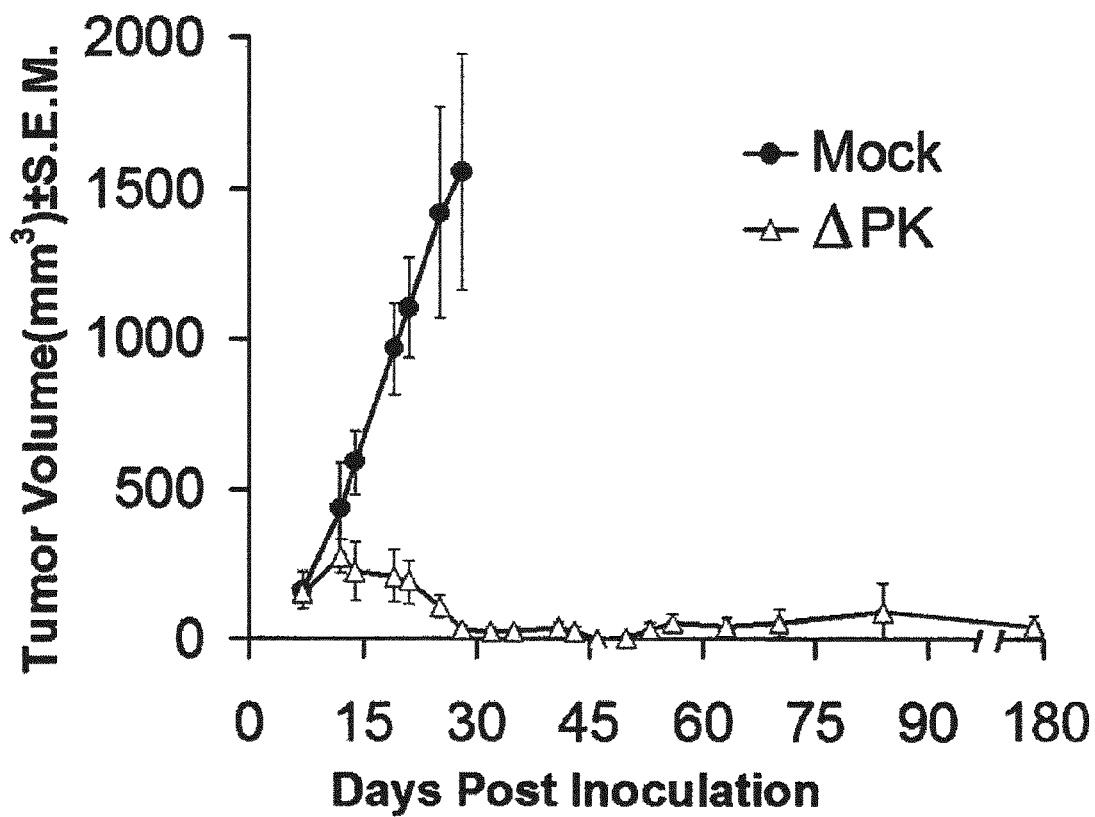

The Animal Care and Use Committee of the University of Maryland School of Medicine approved all the described studies. Six-eight week old male nude mice (Balb/c nu/nu) were obtained from Charles River Laboratories (Wilmington, Mass.). To establish subcutaneous melanoma xenograft models, nude mice were given A2058, A375 or LM melanoma cells ($10^7$ in 100 µl) by subcutaneous injection into both the left and right hind flanks. When the tumors became palpable (approximately 200 mm$^3$ in volume; day 14 for A2058 and day 7 for A375 and LM xenografts), animals were randomly assigned to treatment groups. Treatments consisted of intratumoral injections of partially purified delta-PK ($10^6$ or $10^7$ pfu) in a total volume of 100 µl of cell culture medium or 100 µl of virus-free culture medium (control). The treatment protocol consisted of 4 injections given at weekly intervals (1 injection/week). Every other day, minimum and maximum perpendicular tumor axes were measured with microcalipers and tumor volume was calculated using the formula: volume= [(length×width2)/2]. Animals were maintained in pathogen-free conditions and were euthanized when their tumors reached 1.5 cm in any one direction. Tissues were collected after euthanasia, and processed for virus titration, staining, and immunoblotting. All the mock-treated xenografts evidenced time-dependent growth, with A2058 reaching maximal volume at 42 days (FIG. 8A), A375 at 35 days (FIG. 8B) and LM at 28 days (FIG. 8C), when the mice were sacrificed. Delta-PK caused a significant (p<0.001) decrease in the growth of all the tumors. In the case of the LM xenografts, complete remission was seen for ⅞ tumors (87.5%) followed for 5 months after the last delta-PK injection. The lone recurrent tumor (seen in one animal) did not reach endpoint criteria (1.5 cm in diameter) by this time. Compared to the mock-treated animals, survival was significant (p<0.001), ranging between 80% for A2058 and 100% for LM xenografts (FIG. 8D).

Example 13

Figure 9A:
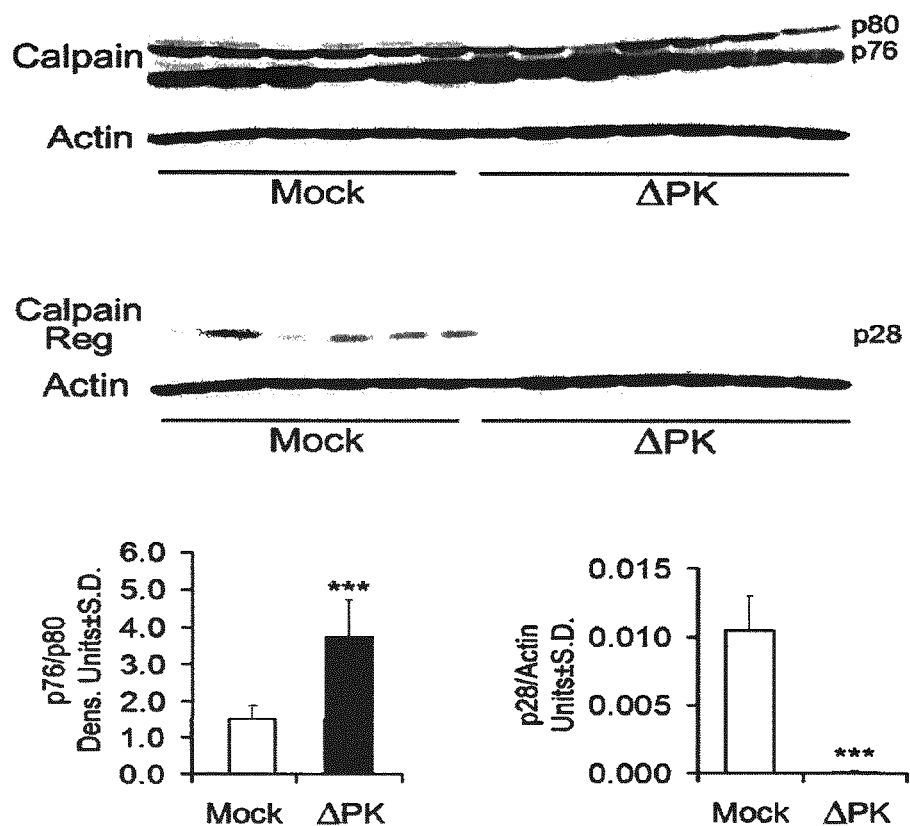
FIG. 9. Calpain and caspases-7 and -3 are activated in delta-PK-treated xenografts. A. A2058 xenograft tissues mock treated or treated with delta-PK were collected 7 days after the last delta-PK injection and extracts were immunoblotted with antibodies to calpain. B. A2058 xenograft tissues mock treated or treated with delta-PK were collected 7 days after the last delta-PK injection and extracts were immunoblotted with antibodies to activated caspase-7. C. A2058 xenograft tissues mock treated or treated with delta-PK were collected 7 days after the last delta-PK injection and extracts were immunoblotted with antibodies pro-caspase-3. Each lane represents a different tumor. Representatives of three replicate experiments are shown for each antibody. Data were quantified by densitometry and results are expressed as densitometric units +/−SD (***p<0.001 vs. Mock).
Figure 9B:
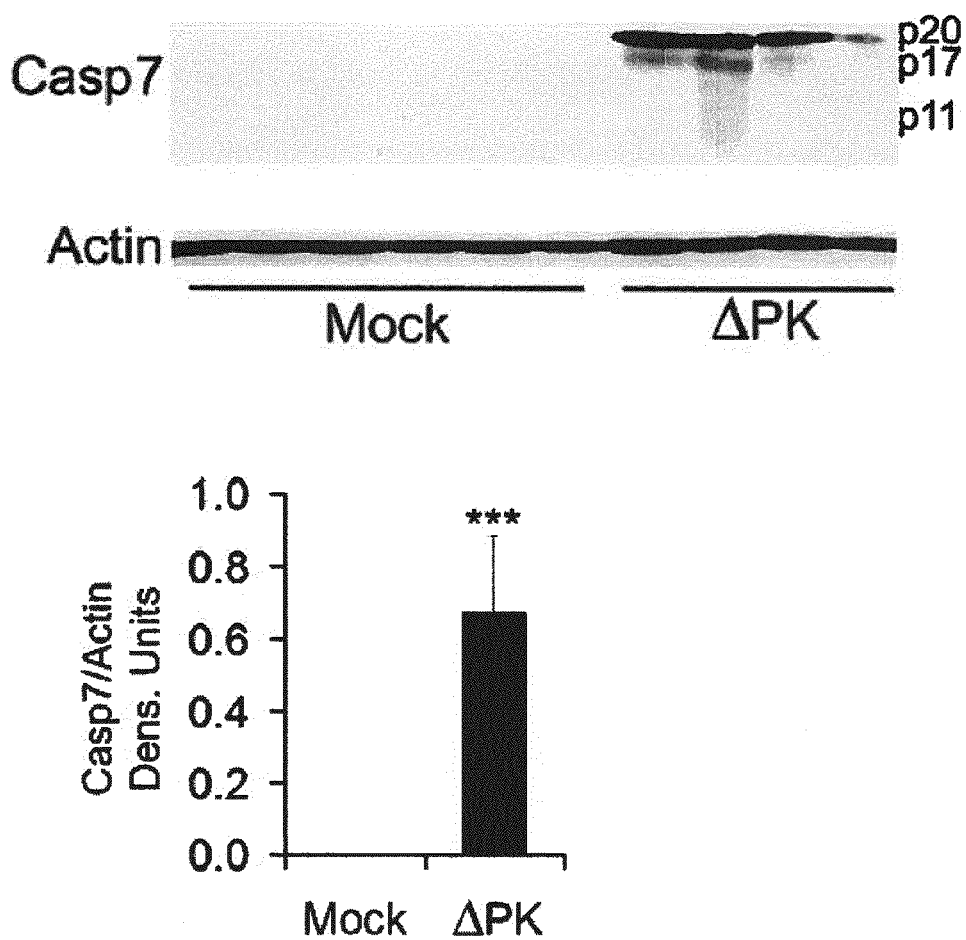
Figure 9C:
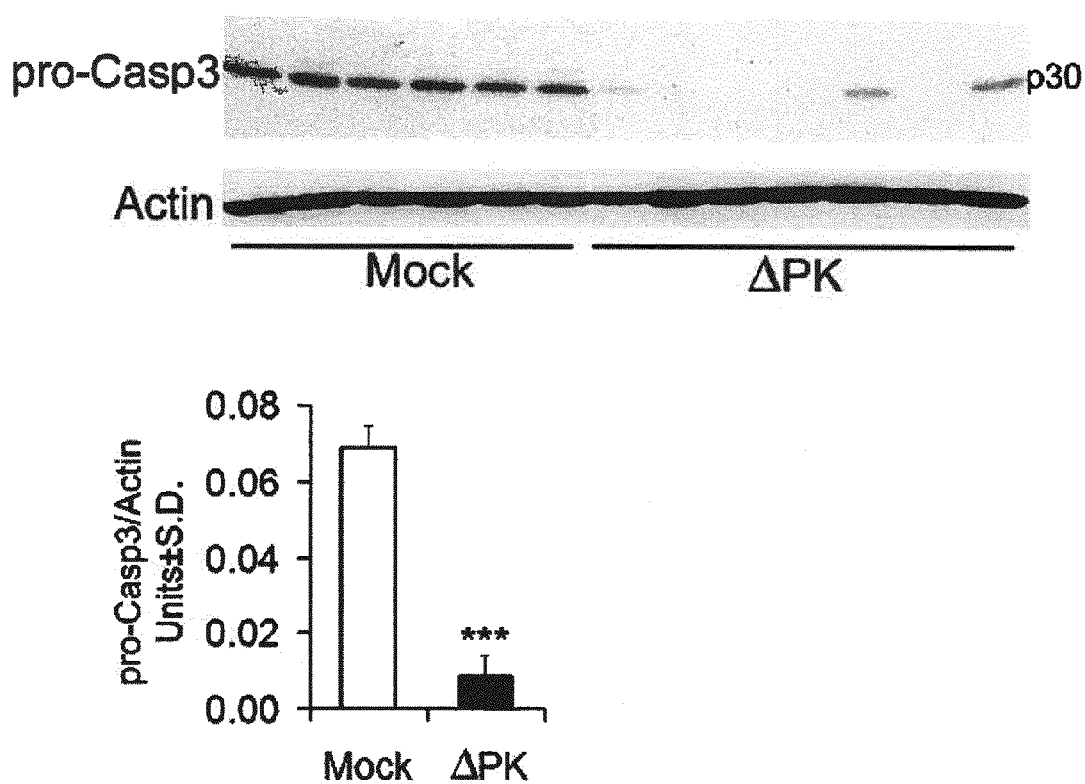

Inhibition of Tumor Growth is Associated with Low Levels of Sustained Viral Replication and Calpain/Caspase Activation Mock and delta-PK-treated xenograft tissues were collected at 7 days after the last delta-PK injection and tissue homogenates were examined for virus replication (infectious virus titers) and activation of calpain and caspase-7 and caspase-3. Virus titers in the delta-PK treated tissues ranged between $2\times10^2$ and $1.5\times10^5$ pfu/ml. In addition, serial sections encompassing the entire tumor mass stained with VP5 antibody with approximately 18-25% VP5+ cells/section, indicative of relatively good virus penetration. Virus was not isolated from the mock-treated tissues and they did not stain with. VP5 antibody. Calpain and caspase-7 and caspase-3 were activated in delta-PK but not mock-treated tissues, as evidenced by: (i) increased ratios of the calpain p76/p80 isoforms; (ii) loss of the p28 regulatory subunit; (iii) presence of the caspase-7p20 and p17 cleavage fragments; and (iv) loss of pro-caspase-3p30 (FIG. 9A-C). Protease activation is due to delta-PK and is not an artifact caused by differences in the tumor microenvironment as evidenced by the fact that activation was not observed in mock-treated tumors and the proteases were also activated by delta-PK in cultured melanoma cells. Collectively, the data indicate that delta-PK replicates at relatively low but sustained levels (still seen at 7 days p.i.) in the melanoma xenografts, where it triggers activation of calpain as well as caspase-7 and caspase-3.

Example 14

Delta-PK Upregulates Beclin-1 and H11/HspB8 in Melanoma Cultures and Xenografts Two series of experiments were done in order to examine whether delta-PK induced cell death is also associated with the activation of other death pathways. In the first series, extracts of A2058 cell cultures mock-infected or infected with delta-PK were immunoblotted with antibodies to the autophagy protein Beclin-1 and the heat shock protein H11/HspB8. Beclin-1 is a critical autophagy protein that is emerging as a potent tumor suppressor and is downregulated in some human tumors (Qu X, Yu J, Bhagat G, Furuya N, Hibshoosh H, Troxel A, et al. Promotion of tumorigenesis by heterozygous disruption of the beclin 1 autophagy gene. *J Clin Invest* 2003; 112: 1809-1820; Miracco C, Cosci E, Oliveri G, Luzi P, Pacenti L, Monciatti I, et al. Protein and mRNA expression of autophagy gene Beclin 1 in human brain tumours. *Int J Oncol* 2007; 30: 429-436). The expression in melanoma is unknown.

Figure 10A:
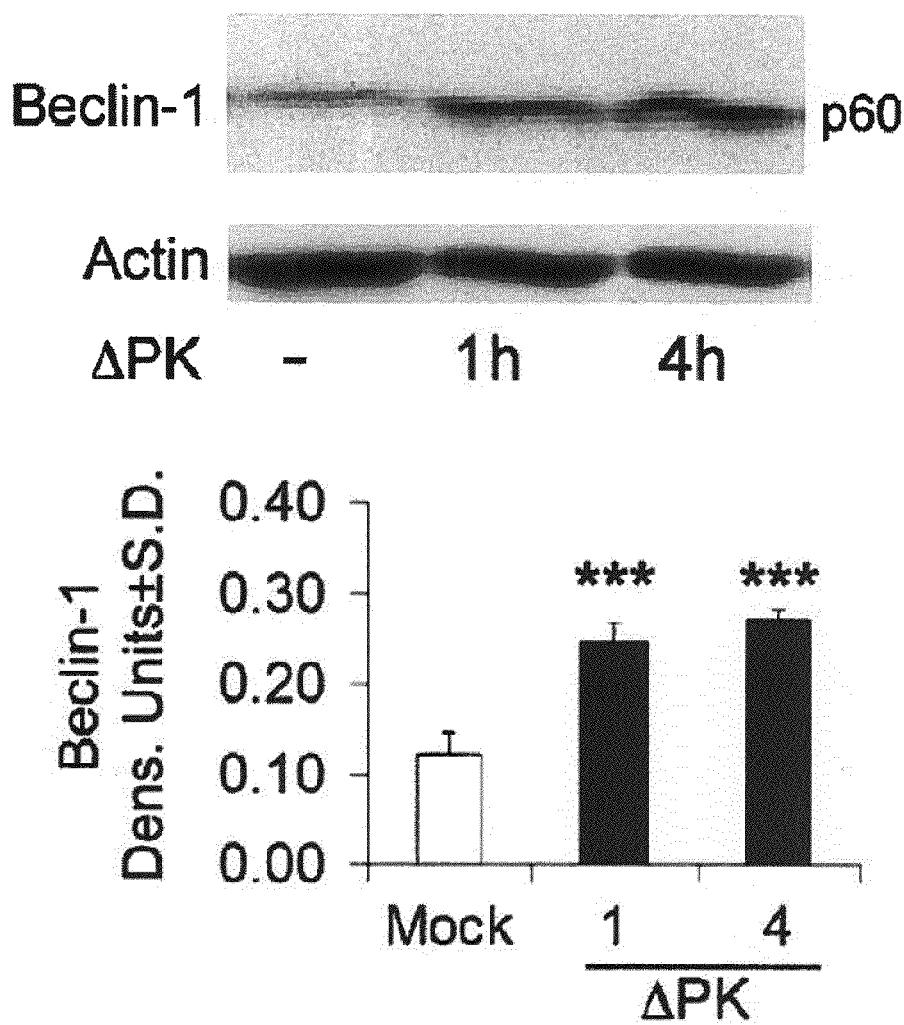
FIG. 10. Beclin-1 and H11/HspB8 are upregulated in delta-PK treated cultures and xenografts. A. A2058 cultures were infected with delta-PK (moi=0.5) and cell extracts obtained at various times p.i. were immunoblotted with antibody to Beclin-1. B. A2058 cultures were infected with delta-PK (moi=0.5) and cell extracts obtained at various times p.i. were immunoblotted with antibody to H-11/HspB8. C. Duplicates of the A2058 xenografts examined for calpain and caspase were immunoblotted with antibody to Beclin-1. D. Duplicates of the A2058 xenografts examined for calpain and caspase were immunoblotted with antibody to H11/HspB8. Data were quantified by densitometry and results are expressed as densitometric units +/−SD (***p<0.001 vs. Mock).
Figure 10B:
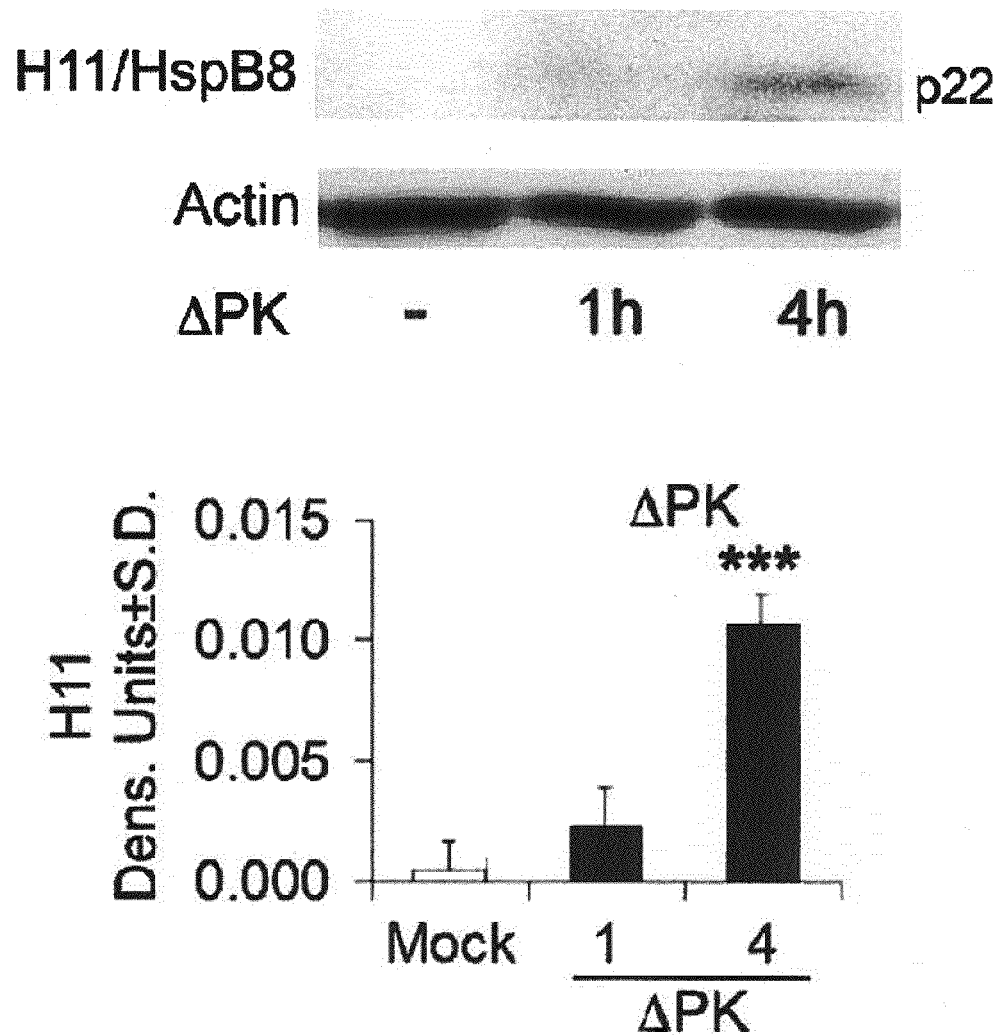
Figure 10C:
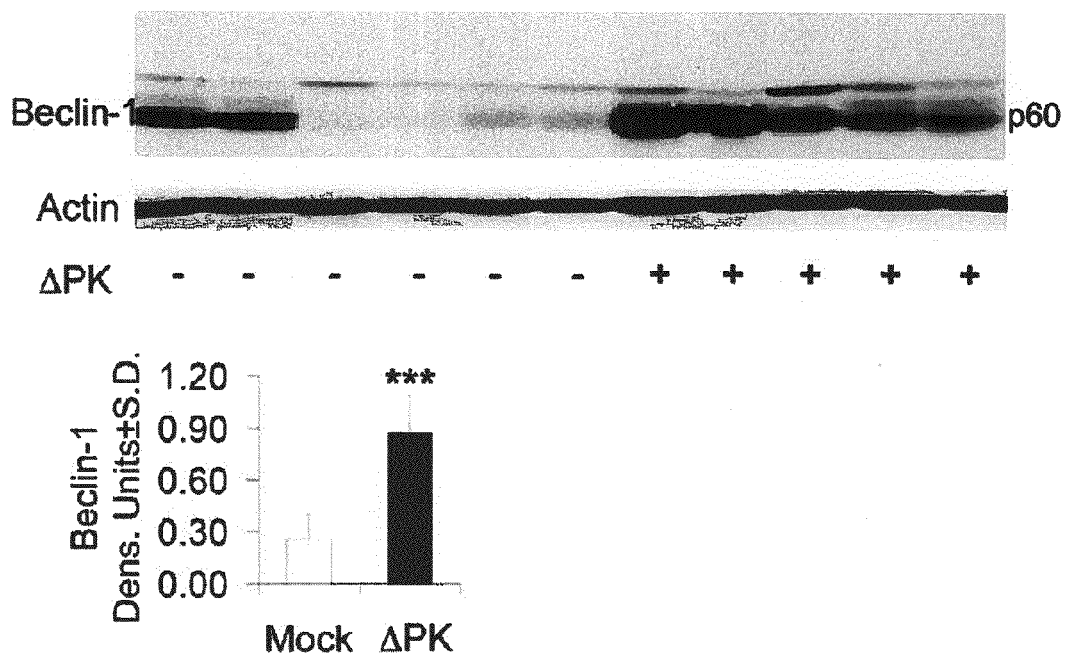
Figure 10D:
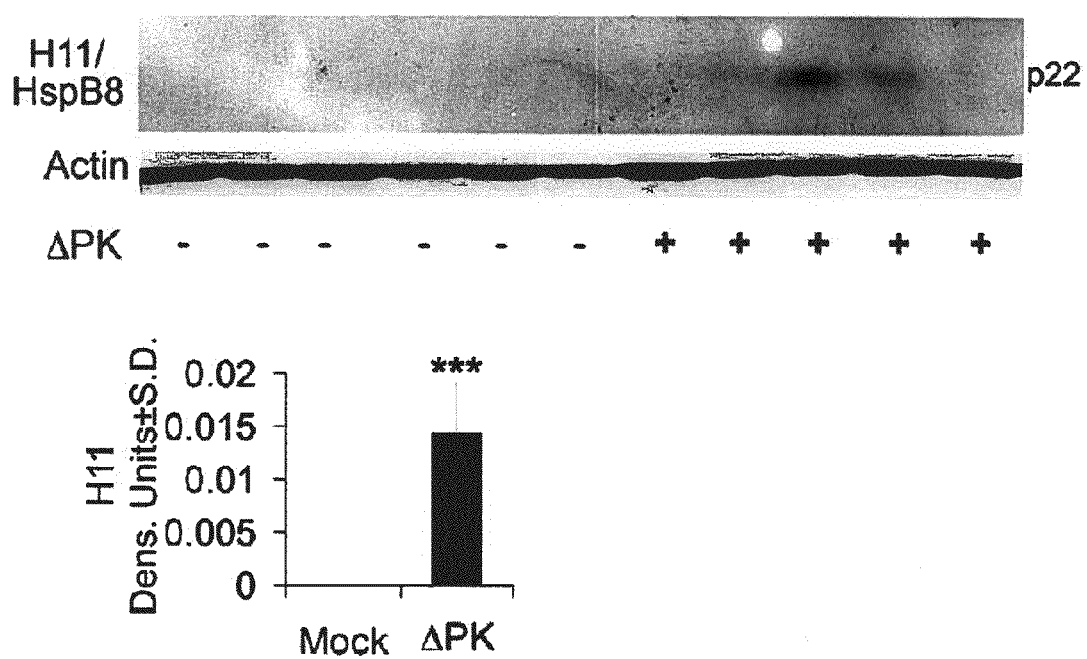

H11/HspB8 is a small heat shock protein that is silenced in 50-60% of melanomas and triggers apoptosis upon forced expression. The data indicate that Beclin-1 was minimally expressed in mock-infected cultures and there was no expression of H11/HspB8 (FIGS. 10A and B). Delta-PK upregulated both Beclin-1 and H11/HspB8, with expression first seen at 1 hr and 4 hrs p.i., respectively. The second series of experiments examined Beclin-1 and H11/HspB8 expression in melanoma xenografts. Beclin-1 expression was inhibited in ⅘ mock-treated tumors and delta-PK caused its upregulation in all the studied xenografts (FIG. 10C). H11/HspB8 expression was also inhibited in the mock treated xenografts and upregulated in ⅗ of those treated with delta-PK (FIG. 10D). Beclin-1 and H11/HspB8 upregulation is not an artifact caused by the tumor microenvironment as evidenced by the fact that it was also seen in cultured melanoma cells and it was not seen in the mock-infected tumors.

Example 15

Caspase-1-related Inflammation is Associated with Delta-PK Oncolysis

Figure 11:
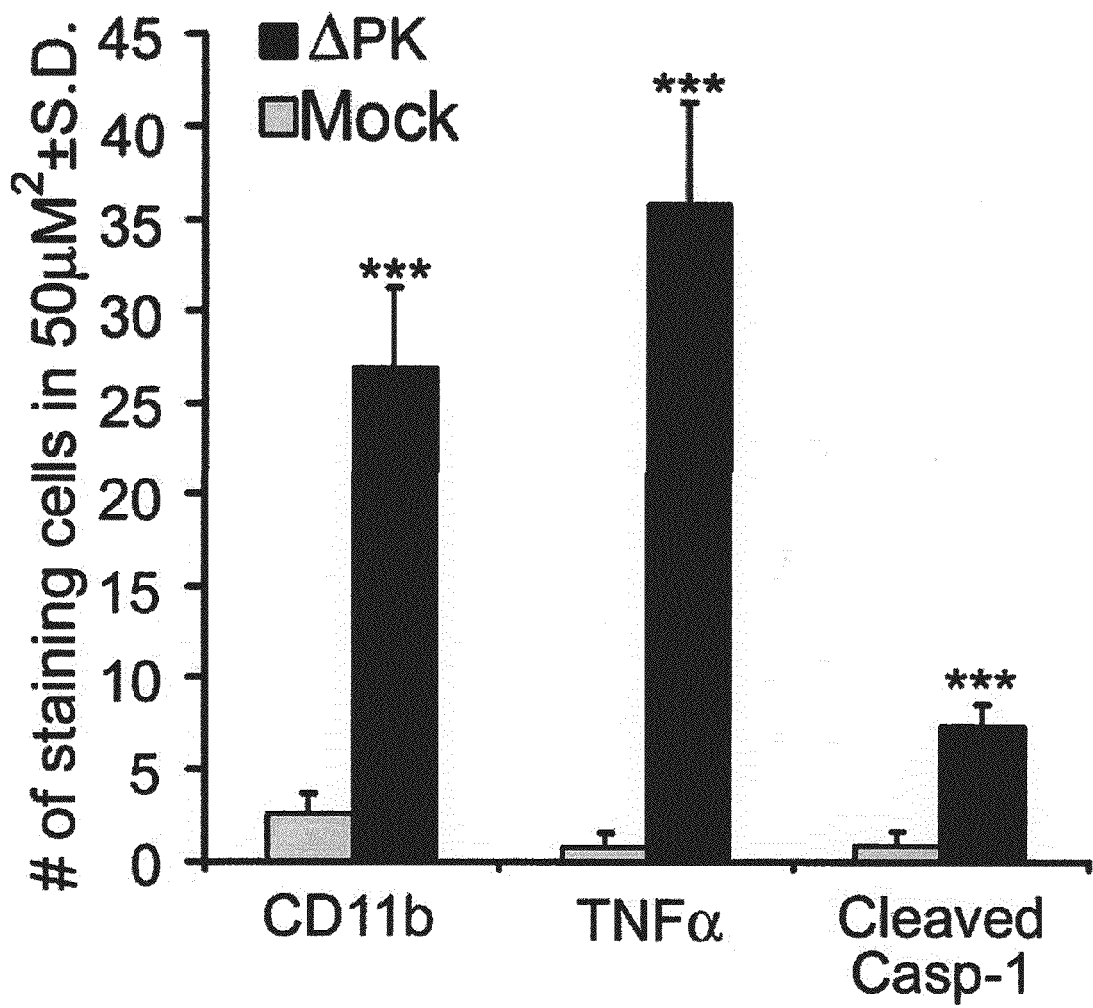
FIG. 11. Delta-PK treated xenografts evidence inflammatory processes. Samples from A2058 xenografts were stained with antibodies to CD11b (macrophage marker), TNF-alpha, and activated caspase-1 (caspase-1p20) by immunohistochemistry and counterstained with Mayer's Heamatoxylin. Cells were counted in three randomly selected fields (50 μm2) and the mean number of positive cells per area was calculated. (***p<0.001 vs. Mock).

Pyroptosis is a caspase-1 dependent inflammatory form of cell death that involves formation of the inflammasome complex and was originally observed in macrophages (Fernandes-Alnemri T, Wu J, Yu J W, Datta P, Miller B, Jankowski W, et al. The pyroptosome: a supramolecular assembly of ASC dimers mediating inflammatory cell death via caspase-1 activation. *Cell Death Differ* 2007; 14: 1590-1604; Yu H B, Finlay B B. The caspase-1 inflammasome: a pilot of innate immune responses. *Cell Host Microbe* 2008; 4: 198-208. Mock- and delta-PK treated xenografts were stained with antibodies to activated caspase-1, CD11b (macrophage marker), and TNF-alpha, which is known to activate caspase-1, trigger apoptosis, and slow the growth of some tumors (Jain N, Sudhakar C, Swamp G. Tumor necrosis factor-alpha-induced caspase-1 gene expression. Role of p73. *FEBS J* 2007; 274: 4396-4407; Villeneuve J, Tremblay P, Vallieres L. Tumor necrosis factor reduces brain tumor growth by enhancing macrophage recruitment and microcyst formation. *Cancer Res* 2005; 65: 3928-3936). Staining with all three antibodies was seen in the delta-PK, but not mock-treated tissues (FIG. 11), indicating that caspase-1 activation and inflammation, both of which are considered markers of pyroptosis are associated with delta-PK induced melanoma oncolysis in vivo.

Example 16

ΔPK Eliminates Melanoma Cells with Stem Cell Markers

Figure 12:
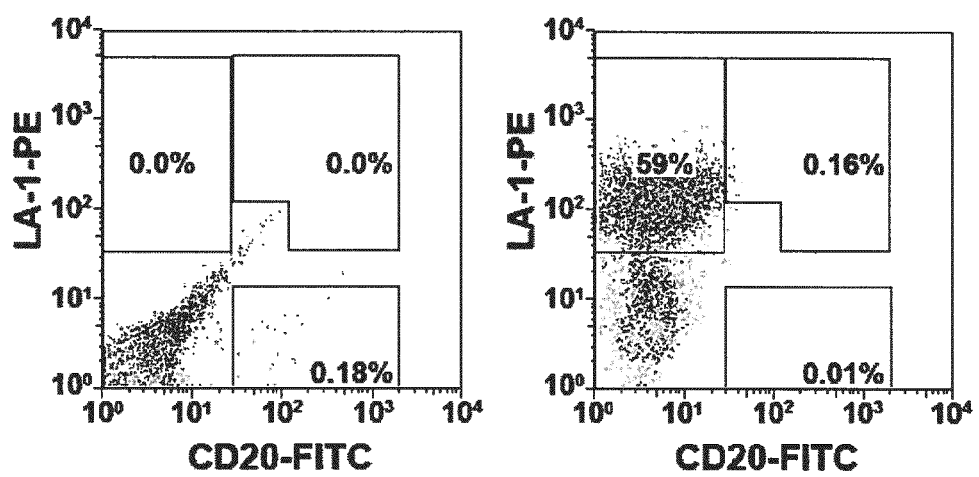
FIG. 12. $\Delta$PK eliminates melanoma cells with stem cell markers. A2058 melanoma cultures infected with $\Delta$PK (multiplicity of infection (moi)=1.0 or mock-infected with adsorption medium were cultured in medium without serum (0%). Cells were harvested and stained 48 hours post infection (p.i.) for flow cytometric analysis. Cells were double stained with FITC-labeled antibody to CD20 and PE-labeled anti-ICP10PK antibody. Gates were drawn based on forward and side scatter and isotype control staining patterns. Isotype controls (IgG1-FITC, IgG1-PE) were subtracted from their counterpart antibodies to obtain the percentages shown.

The ability of virotherapeutic strategies to target and eliminate melanoma stem cells is still unclear. Typically, cancer stem cells (CSC) are thought to be a small subset of tumor cells identified by cell surface marker and/or functional assays. While the very existence of stem cells is still controversial in melanoma, a number of markers were reported to identify melanoma cells with stem cell properties. CD133, CD20, ABCG2, and ABCB5 are among the most frequently cited. To examine whether ΔPK can kill such cells, ΔPK-infected A2058 cultures (48 hrs), were stained with antibodies to CD20, CD133, and ABCG2, and examined by FACS analysis. Anti-IgG1 antibodies served as isotype controls. In mock treated A2058 cells there was a small population of CD20+ cells (0.18%) and a larger proportion of ABCG2+ cells (5.13%), but no CD133+ cells (0.0%), indicating an inherent variability between these 'stem cell markers' and underscoring the potential existence of stem cell heterogeneity. Furthermore, it is not clear from these data whether any particular marker or combination thereof account for functional CSC. Notwithstanding, both the CD20+ and ABCG2+ cells were markedly reduced (0.01%, and 1.42% respectively) in ΔPK-treated melanoma cultures, a reduction of 88% and 72% respectively. This reduction is shown in FIG. 12 for CD20+ cells.

Experimental Design:

A2058 melanoma cultures infected with ΔPK (multiplicity of infection (moi)=1.0 or mock-infected with adsorption medium were cultured in medium without serum (0%). Cells were harvested and stained 48 hours post infection (p.i.) for flow cytometric analysis. Cells were double stained with CD20-FITC and anti-ICP10PK antibody followed by secondary staining with anti-rabbit-PE antibodies. Gates were drawn based on forward and side scatter and isotype control staining patterns. Isotype controls (IgG1-FITC, IgG1-PE) were subtracted from their counterpart antibodies to obtain the percentages shown.

Results:

After subtracting isotype controls, the amount of mock infected A2058 cells staining positive for CD20-FITC was 0.18% of the total cell population. This compares to 0.01% in the ΔPK infected A2058 cells that also exhibit 59% staining with αICP10PK-PE (indicative of infection) at 48 hours p.i. illustrative of infection. See FIG. 12.

Example 17

ΔPK Eliminates Melanoma Stem Cells

To confirm that the loss of cells with stem cell markers is due to the ability of ΔPK to kill cells that function in melanoma growth and resistance (a stem cell trait), we used both the soft agar and spheroid growth assays. Melanoma cultures A375, A2058, MeWo, LN, and OV were mock- or ΔPK-infected (1 pfu/cell; 72 hrs), harvested, counted and triplicate serial dilutions were then assayed for growth under soft agar and under spheroid inducing conditions. The number of colonies formed by the ΔPK-infected cells was drastically reduced in all cultures. The representative data for A2058 demonstrate that of $10^4$ mock infected cells plated, 530±26 colonies were formed (cloning efficiency of 5.4%) and 25±3.6 spheroids were formed (spheroid forming efficiency of 0.25%), illustrating that small populations of cells are capable of exhibiting stem cell growth potential. ΔPK infected cultures were completely unable to form soft agar colonies or spheroids (efficiencies of 0.0067% and 0.0033% respectively). These data indicate that ΔPK eradicates melanoma stem cells, a feature critical to metastatic melanoma therapy.

Figure 13:
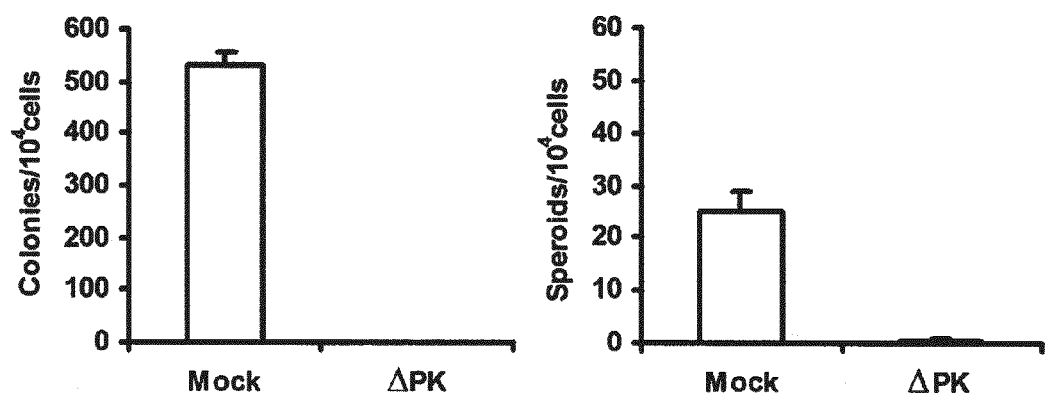
FIG. 13. $\Delta$PK eliminates melanoma stem cells. A2058 melanoma cultures were mock- or $\Delta$PK-infected (1 pfu/cell; 72 hrs), harvested, counted and triplicate serial dilutions were then assayed for growth under soft agar and under spheroid inducing conditions. Colonies were counted when they became 50 μm in diameter. Spheroids were counted when they became 50 cells or larger.

Anchorage independent growth was assessed by the soft agar assay and the spheroid formation assay. Adherent cells were harvested by trypsinization, washed in 1×PBS and counted. In the soft agar assay, wells containing 0.6% agarose in DMEM with 10% FBS. were overlaid with $1\times10^4$ cells/well suspended in 0.3% low melting temperature agarose (SeaPrep agrarose, Lonza, Rockland, Me., USA) in Dulbecco's modified eagle medium (DMEM, Invitrogen) supplemented with a final concentration of 10% FBS. The agarose was allowed to solidify and was then coated with DMEM and 10% FBS. Plates were incubated at 37° C. for 14 days, and colonies (defined as a minimum of 50 μm in diameter) were counted. The assay was performed in triplicate for both mock- and ΔPK-infected cells (moi=1.0, 48 h p.i). See FIG. 13.

In the spheroid formation assay, $1\times10^4$ cells/well were suspended in serum free DMEM supplemented with 20 ng/ml basic fibroblast growth factor (bFGF, R&D Systems) and 20 ng/ml epidermal growth factor (EGF, R&D Systems). Spheroid cultures were grown in a humidified incubator 37° C. with 10% $CO_2$ for 7 days. Spheres defined as containing at least 50 cells were counted. The assay was performed in triplicate for both mock- and ΔPK-infected cells (moi=1.0, 48 h p.i.). See FIG. 13.

Example 18

ΔPK Induces Autophagy

The role of autophagy in cell death is still controversial. The general consensus is that autophagy is a mechanism that promotes or counteracts cell death depending on the cell type, stimulus and conditions. We have already shown that the autophagy protein Beclin 1 is upregulated in ΔPK infected cultures and xenografts, but Beclin 1 may also have functions that are unrelated to autophagy. To examine whether autophagy was increased in ΔPK infected cells, we focused on LC3-I conversion to LC3-II which serves as a marker for autophagosome maturation. Immunoblot analysis showed an enhanced LC3-II/LC3-I ratio in ΔPK- vs. mock-treated cultures. The autophagy inhibitor, 3-Methyl-adenine (3-MA, 5 mM), reversed LC3-I conversion after ΔPK treatment, confirming that ΔPK induces autophagy.

Figure 14A:
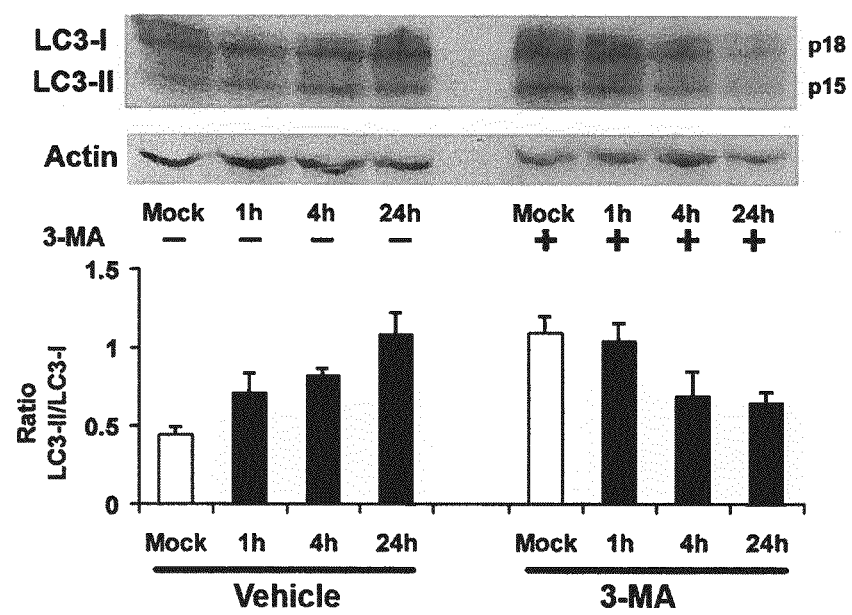
FIG. 14. $\Delta$PK induced autophagy contributes to its ability to cause melanoma cell death. (A) A2058 cells were mock or $\Delta$PK-infected (multiplicity of infection, moi=1.0) with and without the autophagy inhibitor 3-MA and protein extracts were assayed for LC3-I and LC3-II expression by immunoblotting. Data were quantified by densitometric scanning, and results are expressed as LC3-I/LC3-II ratio±s.d. (B). A2058 melanoma cultures were mock or $\Delta$PK-infected (moi=5), cultured in serum-free medium and stained with ethidium homodimer-1 (EtHD-1) at 48 h p.i. Cells were counted in three randomly selected fields (>250 cells) and the mean percentage of staining cells was calculated.

A2058 cells were mock and ΔPK-infected (multiplicity of infection, moi=1.0) with and without the autophagy inhibitor 3-MA. Data were quantified by densitometric scanning, and results are expressed as the ratio of the LC3-I/LC3-II ratio±s.d. See FIG. 14A.

To examine the role of autophagy in ΔPK-induced melanoma cell death, the cultures were mock-infected with PBS or infected with ΔPK in the absence or presence of 3-MA and cell death was determined at 0-72 h p.i. by EtHD-1 staining. ΔPK caused a time-dependent increase in the percentage of EtHD-1+ cells that reached maximal levels at 48 h p.i. (51.1±4.8%,). The percentage of cell death was reduced by 3-MA (37.3±5.2%), indicating that autophagy activation contributes to the ability of ΔPK to kill melanoma cells.

Figure 14B:
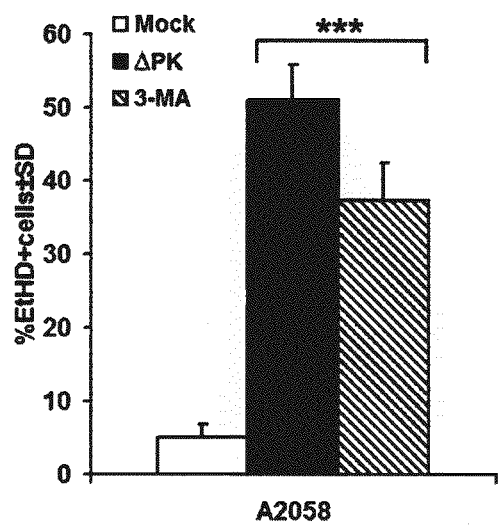

A2058 melanoma cultures were mock or ΔPK-infected (moi=0.5), cultured in serum-free medium and stained with ethidium homodimer-1 (EtHD-1) at 48 h p.i. Cells were counted in three randomly selected fields (>250 cells) and the mean percentage of staining cells was calculated. See FIG. 14B.

Example 19

ΔPK Induces Pyroptosis, a Caspase-1-Dependent Innate Immune Death Pathway

The role of innate immunity and inflammation in the death of melanoma cells is underscored by current therapeutic modalities, such as IL-2, which are the current choice therapies. We did a number of experiments to examine whether these pathways are also activated by ΔPK. In the first series we used array studies as shown below. As shown in FIG. 17 for A2058 cells, ΔPK induced marked upregulation of the inflammatory caspases-1, -4, and -5, and cytokines IL-1α, -1β-6, -8, -12B and LT-α. We confirmed that ΔPK increased caspase-1 activation by immunofluorescent staining of mock- and ΔPK-treated A2058 cultures with antibody to the cleaved fragment. Moreover, ELISA of A2058 cells demonstrated that IL-1β was markedly upregulated following ΔPK infection.

Figure 15D:
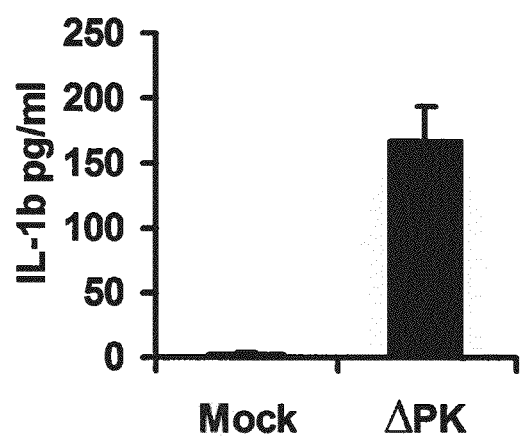
FIG. 15. $\Delta$PK induces pyroptosis, a caspase-1-dependent innate immune death pathway. (A) Total RNA from A2058 cultured cells mock- or $\Delta$PK-infected (0.5 moi) collected at 24 h p.i. was hybridized onto SABiociences, Oligo GeArrays and analyzed using GEArray Expression Analysis Suite 2.0. A heat map of the relative gene expression levels is shown (B) A2058 cells infected as in (A) were fixed then stained with Alexafluor-488-labeled activated caspase-1 antibody (Santa Cruz. Biotech., Santa Cruz, Calif.) Cells were counted in three randomly selected fields (>250 cells) and the percentage of staining cells was calculated relative to total cells identified by 4,6-diamidino-2-phenylindole (DAPI) staining. (C) A2058 xenografts were stained with antibodies to CD11b (macrophage marker), tumor-necrosis factor alpha (TNF-a) or activated caspase-1 (caspase-1p20) by immunohistochemistry and counterstained with Mayer's hematoxylin. (D) Conditioned media collected from mock and $\Delta$PK-infected (moi=1.0, 72 h p.i.) A2058 cells was analyzed for IL-1β production/release by enzyme-linked immununosorbant assay (ELISA).

Collectively, the data indicate that ΔPK induces activation of pyroptosis, which is an additional mechanism in eliminating melanoma tumor burden. See FIG. 15.

Example 20

ΔPK Activates Natural Killer (NK) Cells

Figure 16:
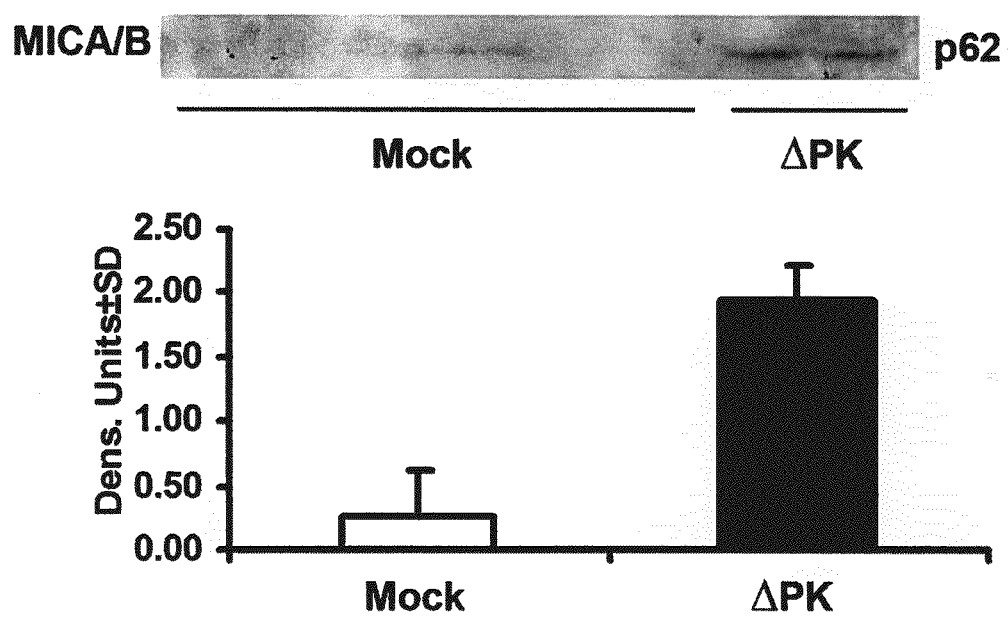
FIG. 16. $\Delta$PK upregulates NK activation marker MICA/B A375 xenograft tissues mock-treated or treated with $\Delta$PK were collected 7 days after the last $\Delta$PK injection and extracts were immunoblotted with antibody to MICA/B. Each lane represents a different tumor. Representatives of three replicate experiments are shown for each antibody. Data were quantified by densitometric scanning and results are expressed as densitometric units.

The NKG2D receptor plays a critical role in the activation of NK cells. Its endogenous ligand, the MHC class I-related, stress inducible surface glycoprotein, MICA is associated with enhanced infiltration of T cells and activation of NK cells. MICA is frequently downregulated at the cell surface of tumor cells by proteolytic cleavage (Helmut R. Salih, Hans-Georg Rammensee, and Alexander Steinle Cutting Edge: Down-Regulation of MICA on Human Tumors by Proteolytic Shedding. J Immunol; 169; 4098-4102). To examine the ΔPK potential to recruit and activate NK cells, we used immunoblotting assays to determine its effect on MICA expression. The data indicate that ΔPK is able to upregulate glycosylated, membrane bound MICA/B in treated tumors, potentially enhancing the initiation of an anti-tumor immune response. See FIG. 16.

All patents and publications mentioned in this specification are indicative of the level of those skilled in the art to which the invention pertains. All patents and publications cited herein are incorporated by reference to the same extent as if each individual publication was specifically and individually indicated as having been incorporated by reference in its entirety.

We claim:

1. A method of treating melanoma, comprising selecting a subject with melanoma and administering to the subject in need thereof an effective amount of a non-fusogenic HSV-2 virus, wherein the non-fusogenic HSV-2 virus lacks protein kinase activity of ICP10 and has a mutation in the ICP10 kinase catalytic domain but retains the transmembrane domain of IPC10.

2. The method of claim 1, wherein the lack of protein kinase activity of ICP10 is the result of a mutation selected from the group consisting of a deletion, an insertion and a point mutation.

3. The method of claim 1, wherein the HSV-2 virus has a deletion in the ICP10 kinase catalytic domain.

4. The method of claim 3, wherein the HSV-2 virus is delta-PK, wherein the delta-PK virus lacks amino acids 106-445 of ICP10.

5. The method of claim 1, further comprising co-administering another anti-cancer agent to the subject.

6. The method of claim 5, wherein the anti-cancer agent is selected from the group consisting of Abraxane, Aldara, Alimta, Aprepitant, Arimidex, Aromasin, Arranon, Arsenic Trioxide, Avastin, Bevacizumab, Bexarotene, Bortezomib, Cetuximab, Clofarabine, Clofarex, Clolar, Dacogen, Dasatinib, Ellence, Eloxatin, Emend, Erlotinib, Faslodex, Femara, Fulvestrant, Gefitinib, Gemtuzumab Ozogamicin, Gemzar, Gleevec, Herceptin, Hycamtin, Imatinib Mesylate, Iressa, Kepivance, Lenalidomide, Levulan, Methazolastone, Mylosar, Mylotarg, Nanoparticle Paclitaxel, Nelarabine, Nexavar, Nolvadex, Oncaspar, Oxaliplatin, Paclitaxel, Paclitaxel Albumin-stabilized Nanoparticle Formulation, Palifermin, Panitumumab, Pegaspargase, Pemetrexed Disodium, Platinol-AQ, Platinol, Revlimid, Rituxan, Sclerosol Intrapleural Aerosol, Sorafenib Tosylate, Sprycel, Sunitinib Malate, Sutent, Synovir, Tamoxifen, Tarceva, Targretin, Taxol, Taxotere, Temodar, Temozolomide, Thalomid, Thalidomide, Topotecan Hydrochloride, Trastuzumab, Trisenox, Vectibix, Velcade, Vidaza, Vorinostat, Xeloda, Zoledronic Acid, Zolinza, Zometa, doxorubicin, adriamycin, bleomycin, daunorubicin, dactinomycin, epirubicin, idarubicin, mitoxantrone, valrubicin, hydroxyurea, mitomycin, fluorouracil, 5-FU, methotrexate, floxuridine, interferon alpha-2b, glutamic acid, plicamycin, 6-thioguanine, aminopterin, pemetrexed, raltitrexed, cladribine, clofarabine, fludarabine, mercaptopurine, pentostatin, capecitabine, cytarabine, carmustine, BCNU, lomustine, CCNU, cytosine arabinoside, cyclophosphamide, estramustine, hydroxyurea, procarbazine, mitomycin, busulfan, medroxyprogesterone, estramustine phosphate sodium, ethinyl estradiol, estradiol, megestrol acetate, methyltestosterone, diethylstilbestrol diphosphate, chlorotrianisene, testolactone, mephalen, mechlorethamine, chlorambucil, chlormethine, ifosfamide, bethamethasone sodium phosphate, dicarbazine, asparaginase, mitotane, vincristine, vinblastine, etoposide, teniposide, Topotecan, IFN-gamma, irinotecan, campto, irinotecan analogs, carmustine, fotemustine, lomustine, streptozocin, carboplatin, oxaliplatin, BBR3464, busulfan, dacarbazine, mechlorethamine, procarbazine, thioTEPA, uramustine, vindesine, vinorelbine, alemtuzumab, tositumomab, methyl aminolevulinate, porfimer, verteporfin, lapatinib, nilotinib, vandetanib, ZD6474, alitretinoin, altretamine, amsacrine, anagrelide, denileukin diftitox, estramustine, hydroxycarbamide, masoprocol, mitotane, and tretinoin.

7. The method of claim 1, further comprising administering a chemotherapeutic agent.

8. The method of claim 7, wherein the chemotherapeutic agent is selected from the group consisting of thiotepa, busulfan, cyclophosphamide, methotrexate, cytarabine, bleomycin, cisplatin, doxorubicin, melphalan, mercaptopurine, vinblastine, paclitaxel and retinoic acid.

9. The method of claim 1, wherein the effective amount is from $1 \times 10^4$ to $4 \times 10^{12}$ PFU of virus per kilogram of body weight of the subject.

10. The method of claim 1, wherein the melanoma is malignant.

11. The method of claim 1, wherein the expression of mutant ICP10 is driven by the ICP10 promoter.

12. The method of claim 1, wherein the non-fusogenic HSV-2 virus has no additional genetic defects.

* * * * *

SEQUENCE LISTING

<160> NUMBER OF SEQ ID NOS: 3

<210> SEQ ID NO 1
<211> LENGTH: 4535
<212> TYPE: DNA
<213> ORGANISM: Herpes Simplex Virus 2

<400> SEQUENCE: 1

```
atggccaacc gccctgccgc atccgccctc gccggagcgc ggtctccgtc cgaacgacag      60
gaaccccggg agcccgaggt cgccccccct ggcggcgacc acgtgttttg caggaaagtc     120
agcggcgtga tggtgctttc cagcgatccc cccgccccg cggcctaccg cattagcgac      180
agcagctttg ttcaatgcgg ctccaactgc agtatgataa tcgacggaga cgtgcgcgc      240 ggtcatttgc gtgacctcga gggcgctacg tccaccggcg ccttcgtcgc gatctcaaac     300
gtcgcagccg gcggggatgg ccgaaccgcc gtcgtgcgc tcggcggaac ctcgggcccg      360
tccgcgacta catccgtggg gacccagacg tccggggagt tcctccacgg gaacccaagg     420
acccccgaac ccaaggacc ccaggctgtc ccccgcccc ctcctccccc ctttccatgg       480
ggccacgagt gctgcgcccg tcgcgatgcc aggggcggcg ccgagaagga cgtcggggcc     540
gcggagtcat ggtcagacgg cccgtcgtcc gactccgaaa cggaggactc ggactcctcg     600
gacgaggata cgggttcgga gacgctgtct cgatcctctt cgatctgggc cgcaggggcg     660
actgacgacg atgacagcga ctccgactcg cggtcgacg actccgtgca gcccgacgtt      720
gtcgttcgtc gcagatggag cgacggcccc gccccgtgg cctttcccaa gccccggcgc      780
cccggcgact cccccggaaa cccggcctg ggcgccggca ccgggccggg ctccgcgacg      840
gacccgcgcg cgtcggccga ctccgattcc gcggcccacg ccgccgcacc ccaggcggac     900
gtggcgccgg ttctggacag ccagcccact gtgggaacgg accccggcta cccagtcccc     960
ctagaactca cgcccgagaa cgcggaggcg gtggcgcggt ttctggggga cgccgtcgac    1020
cgcgagcccg cgctcatgct ggagtacttc tgtcggtgcg cccgcgagga gagcaagcgc    1080 gtgccccac gaaccttcgg cagcgccccc cgcctcacgg aggacgactt tgggctcctg    1140
aactacgcgc tcgctgagat gcgacgcctg tgcctggacc ttccccggt ccccccaaac    1200 gcatacacgc cctatcatct gagggagtat gcgacgcggc tggttaacgg gttcaaaccc    1260
ctggtgcggc ggtccgcccg cctgtatcgc atcctgggg ttctggtcca cctgcgcatc     1320
cgtaccgggg aggcctcctt tgaggaatgg atgcgctcca aggaggtgga cctggacttc    1380
gggctgacgg aaaggcttcg cgaacacgag gcccagctaa tgatcctggc ccaggccctg    1440 aaccctacg actgtctgat ccacagcacc ccgaacacgc tcgtcgagcg ggggctgcag    1500
tcggcgctga agtacgaaga gttttacctc aagcgcttcg gcgggcacta catggagtcc    1560
gtcttccaga tgtacacccg catcgccggg tttctggcgt gccgggcgac ccgcggcatg    1620
cgccacatcg ccctggggcg acaggggtcg tggtgggaaa tgttcaagtt cttttttccac    1680 cgcctctacg accaccagat cgtgccgtcc accccccgcca tgctgaacct cggaacccgc    1740
aactactaca cgtccagctg ctacctggta aaccccagg ccaccactaa ccaggccacc     1800 ctccggggcca tcaccggcaa cgtgagcgcc atcctcgccc gcaacggggg catcgggctg    1860
tgcatgcagg cgttcaacga cgccagcccc ggcaccgcca gcatcatgcc ggccctgaag    1920
gtcctcgact cctggtggc ggcgcacaac aaacagagca cgcgcccac cggggcgtgc     1980 gtgtacctgg aaccctggca cagcgacgtt cgggccgtgc tcagaatgaa gggcgtcctc    2040
```

-continued

```
gccggcgagg aggcccagcg ctgcgacaac atcttcagcg ccctctggat gccggacctg    2100
ttcttcaagc gcctgatccg ccacctcgac ggcgagaaaa acgtcacctg gtccctgttc    2160
gaccgggaca ccagcatgtc gctcgccgac tttcacggcg aggagttcga gaagctgtac    2220
gagcacctcg aggccatggg gttcggcgaa acgatcccca tccaggacct ggcgtacgcc    2280
atcgtgcgca gcgcggccac caccggaagc cccttcatca tgtttaagga cgcggtaaac    2340
cgccactaca tctacgacac gcaaggggcg gccatcgccg gctccaacct ctgcaccgag    2400
atcgtccacc cggcctccaa gcgatccagt ggggtctgca acctgggaag cgtgaatctg    2460
gcccgatgcg tctccaggca gacgtttgac tttgggcggc tccgcgacgc cgtgcaggcg    2520
tgcgtgctga tggtgaacat catgatcgac agcacgctac aacccacgcc ccagtgcacc    2580
cgcggcaacg acaacctgcg gtccatgggc attggcatgc agggcctgca cacggcgtgc    2640
ctcaagatgg gcctggatct ggagtcggcc gagttccggg acctgaacac acacatcgcc    2700
gaggtgatgc tgctcgcggc catgaagacc agtaacgcgc tgtgcgttcg cggggcgcgt    2760
cccttcagcc actttaagcg cagcatgtac cgggccggcc gctttcactg ggagcgcttt    2820
tcgaacgcca gcccgcggta cgagggcgag tgggagatgc tacgccagag catgatgaaa    2880
cacggcctgc gcaacagcca gttcatcgcg ctcatgccca ccgccgcctc ggcccagatc    2940
tcggacgtca gcgagggctt tgcccccctg ttcaccaacc tgttcagcaa ggtgaccagg    3000
gacggcgaga cgctgcgccc caacacgctc ttgctgaagg aactcgagcg cacgttcggc    3060
gggaagcggc tcctggacgc gatggacggg ctcgaggcca agcagtggtc tgtggcccag    3120
gccctgcctt gcctggaccc cgcccacccc ctccggcggt tcaagacggc cttcgactac    3180
gaccaggaac tgctgatcga cctgtgtgca gaccgcgccc cctatgttga tcacagccaa    3240
tccatgactc tgtatgtcac agagaaggcg gacgggacgc tccccgcctc caccctggtc    3300
cgccttctcg tccacgcata taagcgcggc ctgaagacgg ggatgtacta ctgcaaggtt    3360
cgcaaggcga ccaacagcgg ggtgttcgcc ggcgacgaca acatcgtctg cacaagctgc    3420
gcgctgtaag caacagcgct ccgatcgggg tcaggcgtcg ctctcggtcc cgcatatcgc    3480
catggatccc gccgtctccc ccgcgagcac cgaccccccta gatacccacg cgtcgggggc    3540
cggggcggcc ccgattccgg tgtgccccac ccccgagcgg tacttctaca cctcccagtg    3600 cccccgacatc aaccaccttc gctccctcag catcctgaac cgctggctgg agaccgagct    3660
cgtgttcgtg ggggacgagg aggacgtctc caagctctcc gagggcgagc tcggcttcta    3720
ccgctttctg tttgccttcc tgtcggccgc ggacgacctg gtgacggaaa acctgggcgg    3780
cctctccggc ctcttcgaac agaaggacat tcttcactac tacgtggagc aggaatgcat    3840
cgaggtcgtc cactcgcgcg tctacaacat catccagctg gtgctctttc acaacaacga    3900
ccaggcgcgc cgcgcctatg tggcccgcac catcaaccac ccggccattc gcgtcaaggt    3960
ggactggctg gaggcgcggg tgcgggaatg cgactcgatc ccggagaagt tcatcctcat    4020
gatcctcatc gagggcgtct tttttgccgc ctcgttcgcc gccatcgcgt acctgcgcac    4080
caacaacctc ctgcgggtca cctgccagtc gaacgacctc atcagccgcg acgaggccgt    4140
gcatacgaca gcctcgtgct acatctacaa caactacctc gggggccacg ccaagcccga    4200
ggcggcgcgc gtgtaccggc tgtttcggga ggcggtggat atcgagatcg ggttcatccg    4260
atcccaggcc ccgacggaca gctctatcct gagtccgggg gccctggcgg ccatcgagaa    4320
ctacgtgcga ttcagcgcgg atcgcctgct gggcctgatc catatgcagc ccctgtattc    4380
cgcccccgcc cccgacgcca gctttcccct cagcctcatg tccaccgaca aacacaccaa    4440
```

```
cttcttcgag tgccgcagca cctcgtacgc cggggccgtc gtcaacgatc tgtgagggtc    4500
tgggcgccct tgtagcgatg tctaaccgaa ataaa                               4535
```

<210> SEQ ID NO 2
<211> LENGTH: 1142
<212> TYPE: PRT
<213> ORGANISM: Herpes Simplex Virus 2

<400> SEQUENCE: 2

```
Met Ala Asn Arg Pro Ala Ala Ser Ala Leu Ala Gly Ala Arg Ser Pro
1               5                   10                  15

Ser Glu Arg Gln Glu Pro Arg Glu Pro Glu Val Ala Pro Pro Gly Gly
                20                  25                  30

Asp His Val Phe Cys Arg Lys Val Ser Gly Val Met Val Leu Ser Ser
            35                  40                  45

Asp Pro Pro Gly Pro Ala Ala Tyr Arg Ile Ser Asp Ser Ser Phe Val
        50                  55                  60

Gln Cys Gly Ser Asn Cys Ser Met Ile Ile Asp Gly Asp Val Ala Arg
65                  70                  75                  80

Gly His Leu Arg Asp Leu Glu Gly Ala Thr Ser Thr Gly Ala Phe Val
                85                  90                  95

Ala Ile Ser Asn Val Ala Ala Gly Gly Asp Gly Arg Thr Ala Val Val
            100                 105                 110

Ala Leu Gly Gly Thr Ser Gly Pro Ser Ala Thr Thr Ser Val Gly Thr
        115                 120                 125

Gln Thr Ser Gly Glu Phe Leu His Gly Asn Pro Arg Thr Pro Glu Pro
130                 135                 140

Gln Gly Pro Gln Ala Val Pro Pro Pro Pro Pro Pro Phe Pro Trp
                150                 155                 160
145

Gly His Glu Cys Cys Ala Arg Arg Asp Ala Arg Gly Gly Ala Glu Lys
            165                 170                 175

Asp Val Gly Ala Ala Glu Ser Trp Ser Asp Gly Pro Ser Ser Asp Ser
        180                 185                 190

Glu Thr Glu Asp Ser Asp Ser Ser Asp Glu Asp Thr Gly Ser Glu Thr
    195                 200                 205

Leu Ser Arg Ser Ser Ser Ile Trp Ala Ala Gly Ala Thr Asp Asp Asp
210                 215                 220

Asp Ser Asp Ser Asp Ser Arg Ser Asp Ser Val Gln Pro Asp Val
225                 230                 235                 240

Val Val Arg Arg Arg Trp Ser Asp Gly Pro Ala Pro Val Ala Phe Pro
                245                 250                 255

Lys Pro Arg Pro Gly Asp Ser Pro Gly Asn Pro Gly Leu Gly Ala
            260                 265                 270

Gly Thr Gly Pro Gly Ser Ala Thr Asp Pro Arg Ala Ser Ala Asp Ser
        275                 280                 285

Asp Ser Ala Ala His Ala Ala Ala Pro Gln Ala Asp Val Ala Pro Val
    290                 295                 300

Leu Asp Ser Gln Pro Thr Val Gly Thr Asp Pro Gly Tyr Pro Val Pro
305                 310                 315                 320

Leu Glu Leu Thr Pro Glu Asn Ala Glu Ala Val Ala Arg Phe Leu Gly
                325                 330                 335

Asp Ala Val Asp Arg Glu Pro Ala Leu Met Leu Glu Tyr Phe Cys Arg
            340                 345                 350

Cys Ala Arg Glu Glu Ser Lys Arg Val Pro Pro Arg Thr Phe Gly Ser
        355                 360                 365
```

-continued

```
Ala Pro Arg Leu Thr Glu Asp Asp Phe Gly Leu Leu Asn Tyr Ala Leu
370                 375                 380

Ala Glu Met Arg Arg Leu Cys Leu Asp Leu Pro Val Pro Pro Asn
385                 390                 395                 400

Ala Tyr Thr Pro Tyr His Leu Arg Glu Tyr Ala Thr Arg Leu Val Asn
                405                 410                 415

Gly Phe Lys Pro Leu Val Arg Arg Ser Ala Arg Leu Tyr Arg Ile Leu
            420                 425                 430

Gly Val Leu Val His Leu Arg Ile Arg Thr Arg Glu Ala Ser Phe Glu
                435                 440                 445

Glu Trp Met Arg Ser Lys Glu Val Asp Leu Asp Phe Gly Leu Thr Glu
            450                 455                 460

Arg Leu Arg Glu His Glu Ala Gln Leu Met Ile Leu Ala Gln Ala Leu
465                 470                 475                 480

Asn Pro Tyr Asp Cys Leu Ile His Ser Thr Pro Asn Thr Leu Val Glu
                485                 490                 495

Arg Gly Leu Gln Ser Ala Leu Lys Tyr Glu Glu Phe Tyr Leu Lys Arg
            500                 505                 510

Phe Gly His Tyr Met Glu Ser Val Phe Gln Met Tyr Thr Arg Ile
            515                 520                 525

Ala Gly Phe Leu Ala Cys Arg Ala Thr Arg Gly Met Arg His Ile Ala
530                 535                 540

Leu Gly Arg Gln Gly Ser Trp Trp Glu Met Phe Lys Phe Phe His
545                 550                 555                 560

Arg Leu Tyr Asp His Gln Ile Val Pro Ser Thr Pro Ala Met Leu Asn
                565                 570                 575

Leu Gly Thr Arg Asn Tyr Tyr Thr Ser Ser Cys Tyr Leu Val Asn Pro
            580                 585                 590

Gln Ala Thr Thr Asn Gln Ala Thr Leu Arg Ala Ile Thr Gly Asn Val
                595                 600                 605

Ser Ala Ile Leu Ala Arg Asn Gly Gly Ile Gly Leu Cys Met Gln Ala
            610                 615                 620

Phe Asn Asp Ala Ser Pro Gly Thr Ala Ser Ile Met Pro Ala Leu Lys
625                 630                 635                 640

Val Leu Asp Ser Leu Val Ala Ala His Asn Lys Gln Ser Thr Arg Pro
                645                 650                 655

Thr Gly Ala Cys Val Tyr Leu Glu Pro Trp His Ser Asp Val Arg Ala
            660                 665                 670

Val Leu Arg Met Lys Gly Val Leu Ala Gly Glu Glu Ala Gln Arg Cys
                675                 680                 685

Asp Asn Ile Phe Ser Ala Leu Trp Met Pro Asp Leu Phe Phe Lys Arg
690                 695                 700

Leu Ile Arg His Leu Asp Gly Glu Lys Asn Val Thr Trp Ser Leu Phe
705                 710                 715                 720

Asp Arg Asp Thr Ser Met Ser Leu Ala Asp Phe His Gly Glu Glu Phe
                725                 730                 735

Glu Lys Leu Tyr Glu His Leu Glu Ala Met Gly Phe Gly Glu Thr Ile
            740                 745                 750

Pro Ile Gln Asp Leu Ala Tyr Ala Ile Val Arg Ser Ala Ala Thr Thr
            755                 760                 765

Gly Ser Pro Phe Ile Met Phe Lys Asp Ala Val Asn Arg His Tyr Ile
        770                 775                 780

Tyr Asp Thr Gln Gly Ala Ala Ile Ala Gly Ser Asn Leu Cys Thr Glu
785                 790                 795                 800
```

-continued

```
Ile Val His Pro Ala Ser Lys Arg Ser Ser Gly Val Cys Asn Leu Gly
                805                 810                 815
Ser Val Asn Leu Ala Arg Cys Val Ser Arg Gln Thr Phe Asp Phe Gly
            820                 825                 830
Arg Leu Arg Asp Ala Val Gln Ala Cys Val Leu Met Val Asn Ile Met
        835                 840                 845
Ile Asp Ser Thr Leu Gln Pro Thr Pro Gln Cys Thr Arg Gly Asn Asp
    850                 855                 860
Asn Leu Arg Ser Met Gly Ile Gly Met Gln Gly Leu His Thr Ala Cys
865                 870                 875                 880
Leu Lys Met Gly Leu Asp Leu Glu Ser Ala Glu Phe Arg Asp Leu Asn
                885                 890                 895
Thr His Ile Ala Glu Val Met Leu Leu Ala Ala Met Lys Thr Ser Asn
            900                 905                 910
Ala Leu Cys Val Arg Gly Ala Arg Pro Phe Ser His Phe Lys Arg Ser
        915                 920                 925
Met Tyr Arg Ala Gly Arg Phe His Trp Glu Arg Phe Ser Asn Ala Ser
    930                 935                 940
Pro Arg Tyr Glu Gly Glu Trp Glu Met Leu Arg Gln Ser Met Met Lys
945                 950                 955                 960
His Gly Leu Arg Asn Ser Gln Phe Ile Ala Leu Met Pro Thr Ala Ala
                965                 970                 975
Ser Ala Gln Ile Ser Asp Val Ser Glu Gly Phe Ala Pro Leu Phe Thr
            980                 985                 990
Asn Leu Phe Ser Lys Val Thr Arg Asp Gly Glu Thr Leu Arg Pro Asn
        995                 1000                1005
Thr Leu Leu Leu Lys Glu Leu Glu Arg Thr Phe Gly Gly Lys Arg
    1010                1015                1020
Leu Leu Asp Ala Met Asp Gly Leu Glu Ala Lys Gln Trp Ser Val
    1025                1030                1035
Ala Gln Ala Leu Pro Cys Leu Asp Pro Ala His Pro Leu Arg Arg
    1040                1045                1050
Phe Lys Thr Ala Phe Asp Tyr Asp Gln Glu Leu Leu Ile Asp Leu
    1055                1060                1065
Cys Ala Asp Arg Ala Pro Tyr Val Asp His Ser Gln Ser Met Thr
    1070                1075                1080
Leu Tyr Val Thr Glu Lys Ala Asp Gly Thr Leu Pro Ala Ser Thr
    1085                1090                1095
Leu Val Arg Leu Leu Val His Ala Tyr Lys Arg Gly Leu Lys Thr
    1100                1105                1110
Gly Met Tyr Tyr Cys Lys Val Arg Lys Ala Thr Asn Ser Gly Val
    1115                1120                1125
Phe Ala Gly Asp Asp Asn Ile Val Cys Thr Ser Cys Ala Leu
    1130                1135                1140
```

<210> SEQ ID NO 3
<211> LENGTH: 21
<212> TYPE: DNA
<213> ORGANISM: Herpes Simplex Virus 2

<400> SEQUENCE: 3
ccccttcatc atgtttaagg a                                              21